US009997891B2

United States Patent
Cable et al.

(10) Patent No.: US 9,997,891 B2
(45) Date of Patent: Jun. 12, 2018

(54) WIDELY TUNABLE SHORT CAVITY LASER

(71) Applicants: Thorlabs, Inc., Newton, NJ (US); Praevium Research, Inc., Santa Barbara, CA (US)

(72) Inventors: Alex Ezra Cable, Newton, NJ (US); Vijaysekhar Jayaraman, Goleta, CA (US); Benjamin Michael Potsaid, Cambridge, MA (US)

(73) Assignees: Thorlabs, Inc., Newton, NJ (US); Praevium Research, Inc., Santa Barbara, CA (US)

( * ) Notice: Subject to any disclaimer, the term of this patent is extended or adjusted under 35 U.S.C. 154(b) by 0 days. days.

(21) Appl. No.: 15/600,074

(22) Filed: May 19, 2017

(65) Prior Publication Data
US 2017/0256910 A1    Sep. 7, 2017

Related U.S. Application Data

(63) Continuation of application No. 13/952,554, filed on Jul. 26, 2013, now Pat. No. 9,843,159.
(Continued)

(51) Int. Cl.
*H01S 5/0683*    (2006.01)
*H01S 3/10*    (2006.01)
(Continued)

(52) U.S. Cl.
CPC ........ *H01S 5/0683* (2013.01); *G01B 9/02004* (2013.01); *G01B 9/02091* (2013.01);
(Continued)

(58) Field of Classification Search
CPC .. H01S 3/034; H01S 3/05–3/06; H01S 3/086; H01S 3/101
See application file for complete search history.

(56) References Cited

U.S. PATENT DOCUMENTS 5,331,658 A    7/1994  Shieh et al.
5,631,736 A    5/1997  Thiel et al.
(Continued)

FOREIGN PATENT DOCUMENTS

CN    2738507 Y    11/2005
CN    101796646 A    8/2010
(Continued)

OTHER PUBLICATIONS

Japanese Notice of Reasons for Rejection, issued by the Japanese Patent Office dated May 2, 2017 for corresponding Japan application No. 2015-524490.
(Continued)

*Primary Examiner* — Dung Nguyen
(74) *Attorney, Agent, or Firm* — Myers Wolin, LLC

(57) ABSTRACT

A tunable source includes a short-cavity laser optimized for performance and reliability in SSOCT imaging systems, spectroscopic detection systems, and other types of detection and sensing systems. The short cavity laser has a large free spectral range cavity, fast tuning response and single transverse, longitudinal and polarization mode operation, and includes embodiments for fast and wide tuning, and optimized spectral shaping. Disclosed are both electrical and optical pumping in a MEMS-VCSEL geometry with mirror and gain regions optimized for wide tuning, high output power, and a variety of preferred wavelength ranges; and a semiconductor optical amplifier, combined with the short-cavity laser to produce high-power, spectrally shaped operation. Several preferred imaging and detection systems make use of this tunable source for optimized operation are also disclosed.

22 Claims, 19 Drawing Sheets

Related U.S. Application Data

(60) Provisional application No. 61/676,712, filed on Jul. 27, 2012.

(51) Int. Cl.

| | | |
|---|---|---|
| *H01S 3/105* | (2006.01) | |
| *H01S 5/10* | (2006.01) | |
| *H01S 5/34* | (2006.01) | |
| *G01N 21/25* | (2006.01) | |
| *G01N 21/27* | (2006.01) | |
| *H01S 5/06* | (2006.01) | |
| *H01S 5/04* | (2006.01) | |
| *G01B 9/02* | (2006.01) | |
| *H01S 3/139* | (2006.01) | |
| *H01S 5/028* | (2006.01) | |
| *H01S 5/042* | (2006.01) | |
| *H01S 5/343* | (2006.01) | |
| *H01S 5/00* | (2006.01) | |
| *H01S 5/0687* | (2006.01) | |
| *H01S 5/183* | (2006.01) | |
| *G01N 21/47* | (2006.01) | |
| *G01N 21/39* | (2006.01) | |

(52) U.S. Cl.
CPC ......... *G01N 21/255* (2013.01); *G01N 21/272* (2013.01); *H01S 3/105* (2013.01); *H01S 3/10015* (2013.01); *H01S 3/10061* (2013.01); *H01S 3/1396* (2013.01); *H01S 5/0071* (2013.01); *H01S 5/028* (2013.01); *H01S 5/041* (2013.01); *H01S 5/042* (2013.01); *H01S 5/0607* (2013.01); *H01S 5/1039* (2013.01); *H01S 5/183* (2013.01); *H01S 5/18355* (2013.01); *H01S 5/18361* (2013.01); *H01S 5/18366* (2013.01); *H01S 5/34* (2013.01); *H01S 5/34306* (2013.01); *H01S 5/34313* (2013.01); *G01N 21/4795* (2013.01); *G01N 2021/399* (2013.01); *G01N 2201/0612* (2013.01); *H01S 5/0078* (2013.01); *H01S 5/0687* (2013.01); *H01S 5/18311* (2013.01); *H01S 5/18372* (2013.01); *H01S 2301/02* (2013.01)

(56) References Cited

U.S. PATENT DOCUMENTS

| | | | |
|---|---|---|---|
| 5,805,626 | A | 9/1998 | Komatsu |
| 5,991,326 | A | 11/1999 | Yuen et al. |
| 6,154,471 | A | 11/2000 | Jin et al. |
| 6,263,002 | B1 | 7/2001 | Hsu et al. |
| 6,594,022 | B1 | 7/2003 | Watterson et al. |
| 7,468,997 | B2 | 12/2008 | Jayaraman et al. |
| 7,671,997 | B2 | 3/2010 | Jayaraman et al. |
| 7,675,956 | B2 | 3/2010 | Maeda et al. |
| 8,212,235 | B2 | 7/2012 | Wang et al. |
| 8,256,298 | B2 | 9/2012 | Suijlen et al. |
| 8,861,218 | B2 | 10/2014 | Smith et al. |
| 2003/0031221 | A1* | 2/2003 | Wang .................. H01S 5/18366 372/45.01 |
| 2003/0081875 | A1 | 5/2003 | Kochergin et al. |
| 2004/0071180 | A1 | 4/2004 | Wang |
| 2004/0076198 | A1 | 4/2004 | Spoonhower et al. |
| 2004/0190584 | A1 | 9/2004 | Spoonhower et al. |
| 2004/0202399 | A1 | 10/2004 | Kochergin et al. |
| 2005/0047727 | A1 | 3/2005 | Shin et al. |
| 2006/0268398 | A1 | 11/2006 | Cole et al. |
| 2007/0036186 | A1 | 2/2007 | Corzine et al. |
| 2007/0036189 | A1 | 2/2007 | Hori et al. |
| 2007/0280703 | A1 | 12/2007 | Taverner et al. |
| 2008/0159468 | A1 | 7/2008 | Chong |
| 2009/0030348 | A1 | 12/2009 | Bond et al. |
| 2009/0303487 | A1 | 12/2009 | Bond et al. |
| 2010/0078577 | A1 | 4/2010 | Moriya et al. |
| 2010/0157295 | A1 | 6/2010 | Ko et al. |
| 2011/0032605 | A1 | 2/2011 | Kliner et al. |
| 2011/0192978 | A1 | 8/2011 | Jeon et al. |
| 2012/0093189 | A1 | 4/2012 | Fattal et al. |

FOREIGN PATENT DOCUMENTS

| | | |
|---|---|---|
| CN | 102032970 A | 4/2011 |
| CN | 102256893 A | 11/2011 |
| EP | 1225669 A1 | 7/2002 |
| EP | 2133686 A1 | 12/2009 |
| JP | H1170084 A | 7/1989 |
| JP | H09251176 A | 9/1997 |
| JP | 2000244057 A | 9/2000 |
| JP | 2002500446 A | 1/2002 |
| JP | 2003501837 A | 1/2003 |
| JP | 2003046174 A | 2/2003 |
| JP | 2003523092 A | 7/2003 |
| JP | 2004212638 A | 7/2004 |
| JP | 2005039102 A | 2/2005 |
| JP | 2005079588 A | 3/2005 |
| JP | 2007278868 A | 10/2007 |
| JP | 2008244060 A | 10/2008 |
| JP | 2010145392 A | 7/2010 |
| JP | 2010186735 A | 8/2010 |
| JP | 2011164578 A | 8/2011 |
| WO | 9934484 A2 | 7/1999 |
| WO | 0075989 A1 | 12/2000 |
| WO | 0076039 A1 | 12/2000 |
| WO | 0159895 A1 | 8/2001 |
| WO | 0167156 A2 | 9/2001 |
| WO | 01067156 A2 | 9/2001 |
| WO | 02075263 A1 | 9/2002 |
| WO | 2009140614 A2 | 11/2009 |
| WO | 2010142039 A1 | 12/2010 |
| WO | 2012099914 A1 | 7/2012 |
| WO | 2014018945 A9 | 2/2015 |

OTHER PUBLICATIONS

V. Jayaraman, et al., and "High-sweep-rate. 1310 Nm MEMS-VCSEL with 150 nm continuous tuning range", Electronics Letters, vol. 48, No. Jul. 5, 14-2012, p. 867-869.

Japanese Notice of Reasons for Rejection, issued by the Japanese Patent Office dated May 2, 2017 for corresponding Japan application No. 2015-524491.

Chinese Notice of First Office Action, dated Oct. 27, 2016, for corresponding China application No. 201380045781.X with English translation.

Chinese Notice of First Office Action, dated Nov. 2, 2016, for corresponding China application No. 201380040021.X with English translation.

Chinese Notice of First Office Action, dated Nov. 28, 2016, for corresponding China application No. 201380046414.1 with English translation.

Chinese Notice of First Office Action, dated Dec. 5, 2016, for corresponding China application No. 201380039767.9 with English translation.

Chinese Notice of First Office Action, dated Dec. 29, 2016, for corresponding China application No. 201380039785.7 with English translation.

Corzine, Scott W., et al. "Design of Fabry-Perot Surface-Emitting Lasers with a Periodic Gain Structure", IEEE Journal of Quantum Electronics, the 25th Volume, No. 6 ,p. 1513-1524, (Jun. 30, 1989).

Chinese Notice of Second Office Action, dated May 11, 2017, for corresponding China application No. 201380045781.X with English translation.

Chinese Notice of Second Office Action, dated May 15, 2017, for corresponding China application No. 201380046414.1 with English translation of first 2 pages.

Japanese Notice of Reasons for Rejection, issued by the Japanese Patent Office dated Jul. 11, 2017 and English machine translation for corresponding Japan application No. 2015-524493.

(56) References Cited

OTHER PUBLICATIONS

Chinese Notice of Second Office Action, dated Jun. 30, 2017 with English translation, for corresponding China application No. 201380039785.7.
Cole, Garrett, D; et al. "MEMS-tunable vertical-cavity SOAs"; IEEE Journal of Quantum Electronics (vol. 41, Issue: 3, Mar. 2005); DOI: 10.1109/JQE.2004.841496.
Chinese Notice of Second Office Action, dated Jul. 4, 2017 with English translation, for corresponding China application No. 201380040021.X.
Chinese Notice of Second Office Action, dated Jul. 5, 2017 with English translation, for corresponding China application No. 201380039767.9.
Japanese Notice of Reasons for Rejection, dated Jun. 27, 2017 with English translation, for corresponding Japan application No. 2015-524495.
Japanese Notice of Reasons for Rejection, dated Jul. 11, 2017 with Full English translation, for corresponding Japan application No. 2015-524493.
Japanese Notice of Reasons for Rejection, dated Jul. 19, 2017 with Full English translation, for corresponding Japan application No. 2015-524494.
International Preliminary Report on Patentability dated Feb. 2, 2015 in corresponding international application No. PCT/US2013/052415.
International Preliminary Report on Patentability dated Feb. 5, 2015, with written opinion of the International Searching Authority dated Nov. 8, 2013, for corresponding International Application No. PCT/US2013/052411.
International Preliminary Report on Patentability with written opinion, dated Feb. 5, 2015, for corresponding International Application No. PCT/US2013/052412.
International Preliminary Report on Patentability dated Feb. 5, 2015, with written opinion of the International Searching Authority dated Nov. 7, 2013, for corresponding International Application No. PCT/US2013/052416.
International Search Report dated Nov. 7, 2013, for corresponding International Application No. PCT/US2013/052416.
International Preliminary Report on Patentability dated Feb. 5, 2015, with written opinion of the International Searching Authority dated Nov. 22, 2013, for corresponding International Application No. PCT/US2013/052418.
International Search Report dated Nov. 19, 2013, for corresponding International Application No. PCT/US2013/052411.
International Search Report dated Nov. 7, 2013, for corresponding International Application No. PCT/US2013/052412.
International Search Report dated Nov. 22, 2013, for corresponding International Application No. PCT/US2013/052418.
International Search Report dated Nov. 7, 2013, for corresponding International Application No. PCT/US2013/052415.
Extended European Search Report including the European search opinion issued for corresponding European Patent Application No. EP 13823861.3 dated Apr. 22, 2016.
Bond T C et al; "Photonic MEMS for NIR in-situ Gas Detection and Identification", Sensors, 2007 IEEE, PI, Oct. 28, 2007 (Oct. 28, 2007), pp. 1368-1371, XP031221326, ISBN: 978-1-4244-1261-7.
Extended European search report including the European search opinion issued for corresponding European Patent Application No. EP13823016.4 dated May 30, 2016.
Sugihwo, Fredy et al. "Micromachined widely tunable vertical cavity laser diodes." Microelectromechanical Systems, Journal of 7.1 (1998): 48-55.
L. A. Callaghan et al. "Beam-supported AlN thin film bulk acoustic resonators" IEEE Transactions on Ultrasonics, Ferroelectrics, and Frequency Control; Year: 2006, vol. 53, Issue: 5; pp. 1001-1007, DOI: 10.1109/TUFFC.2006.1632689.
Cole, G D., et al: "Short-wavelength MEMS-tunable VCSELs." Optics Express 16, No. 20 (2008): 16093-16101.
Extended European search report including the European search opinion issued for corresponding European Patent Application No. EP13823419.0 dated Apr. 29, 2016.
Extended European search report including the European search opinion issued for corresponding European Patent Application No. EP13822317.7 dated Apr. 29, 2016.
Rizzi, F et al: "(In, Ga) N / GaN microcavities with double dielectric mirrors fabricated by selective removal of an (Al, In) N sacrificial layer", Applied Physics Letters, American Institute of Physics, 2 Huntington Quadrangle, Melville, NY 11747, vol. 90, No. 11, Mar. 15, 2007 (Mar. 15, 2007), pp. 111112-111112, XP012093541, ISSN: 0003-6951,DOI: 10.1063/1.2712786.
Yoo B-S et al: "Low threshold current density InGaAs surface-emitting lasers with periodic gain active structure", Electronics Letters, IEE Stevenage, GB vol. 30, No. 13, Jun. 23, 1994 (Jun. 23, 1994), pp. 1060-1061, XP006000713, ISSN: 0013-5194, DOI: 10.1049/EL:19940719.
Wang J J et al: "High-Performance Nanowire-grid Polarizers", Optics Letters, Optical Society of America, US, vol. 30, No. 2, Jan. 15, 2005 (Jan. 15, 2005), pp. 195-197, XP 008122710, ISSN: 0146-9592, DOI: 10.1364/OL.30.000195.
Burroughs S et al: "Complete polarization mode control of long-wavelength tunable vertical-cavity surface-emilting lasers over 65-nm tuning, up to 14-mW output power", IEEE Journal of Quantum Electronics, IEEE Service Center, Piscataway, NJ, USA, vol. 39, No. 9, Sep. 1, 2003 (Sep. 1, 2003), pp. 1037-1048, XP011100308, ISSN: 0018-9197, DOI: 10.1109/JQE.2003.816110.
Extended European search report including the European search opinion issued for corresponding European Patent Application No. EP13822215.3 dated Apr. 22, 2016.
Japanese Notice of Reasons for Rejection, dated Sep. 12, 2017 with English machine translation, for corresponding Japan application No. 2015-524490.
Garrett D. Cole, et al.,"Dynamic Characterization of MEMS-Tunable Vertical-Cavity SOAs", and Proceedings of the 2005 IEEE/LEOS. International Conference on Optical MEMS and Their Applications, Oulu, Finland, Aug. 1, 2005, p. 99-100.
3797-12 (THOR 3794CCN)-State Intellectual Property Office of the P.R.C. Chinese Notice of Third Office Action, dated Jan. 10, 2018 with English translation, for corresponding China application No. 201380039767.9.
3797-12 (THOR 3794EJP)-Japan Patent Office Japanese Notice of Reasons for Rejection, dated Jan. 31, 2018 with English machine translation, for corresponding Japan application No. 2015-524493.
3797-12 (THOR 3794CJP)-Japan Patent Office Japanese Decision to Grant dated Jan. 31, 2018 for corresponding Japan application No.: 2015-524495.
3797-12 (THOR 3794BCN)-State Intellectual Property Office of the P.R.C. Chinese Notice of Third Office Action, dated Jan. 3, 2018 with English translation, for corresponding China application No. 201380040021.X.
Hsu et al, "Characterization of microsecond tuning speed in miniature fiber Fabry-Perot tunable filters", Optical Fiber Communications Conference 1995 OSA Technical Digest Series (Optical Society of America, 1995), vol. 8, p. 18-19, OFC '95 Technical Digest, TuE4.
3797-12 (THOR 3794ACN)-State Intellectual Property Office of the P.R.C. Chinese Notice of Allowance, dated Jan. 9, 2018 with English translation, for corresponding China application No. 2013800397857.

* cited by examiner

2510. Wafer bonding

Bonded Interface

2520. InP substrate removal

2530. AR coating and bottom actuator contact deposition/patterning

Bottom actuator contact

AR coating

Holes for Mirror oxidation

2540. Deposit germanium sacrificial layer pattern curved surface

2550. Membrane deposition, top contact deposition and patterning, and mirror deposition and patterning 2560. Germanium undercutting for release of suspended membrane A. Multiplexing configuration B. TCSL Pump energy C. TSCL Wavelength D. Multiplexed output wavelength Legend:
———————— TSCL 1
– – – – – – – – TSCL 2

WIDELY TUNABLE SHORT CAVITY LASER

CROSS REFERENCES TO RELATED APPLICATIONS

This application is a continuation of U.S. patent application Ser. No. 13/952,554, filed on Jul. 26, 2013, which claims the benefit of U.S. Provisional Patent Application No. 61/676,712 filed on Jul. 27, 2012. The disclosures of U.S. patent application Ser. No. 13/952,554 and U.S. Provisional Patent Application 61/676,712 are hereby incorporated by reference.

FIELD OF THE INVENTION

The present invention relates to tunable lasers, widely tunable lasers, wavelength swept sources, amplified tunable lasers, rapidly tuned lasers, and optical systems enabled by these devices.

BACKGROUND

Widely and rapidly tunable lasers are important for a variety of detection, communication, measurement, therapeutic, sample modification, and imaging systems. For example, swept source optical coherence tomography (SSOCT) systems employ repetitively swept tunable lasers to generate subsurface microstructural images of a wide range of materials. In SS-OCT, wide tuning range translates to higher axial measurement resolution, and higher tuning speed enables real-time acquisition of large data sets. In addition, variable tuning speed enables trading off imaging range and resolution as required for different applications. Lastly, long coherence length, which is equivalent to narrow linewidth, enables long imaging range. Another example of a system which requires rapidly and widely tunable lasers is transient gas spectroscopy as, for example, described in (Stein, B. A., Jayaraman, V. Jiang, J. J, et al., "Doppler-limited H2O and HF absorption spectroscopy by sweeping the 1321-1354 nm range at 55 kHz repetition rate using a single-mode MEMS-tunable VCSEL," Applied Physics B: Lasers and Optics 108(4), 721-5 (2012)). In gas spectroscopy, tuning speed enables characterization of time-varying processes, such as in engine thermometry. Narrow spectral width enables resolution of narrow absorption features, such as those that occur at low gas temperatures. Other transient spectroscopic applications include monitoring of explosive or other non-repetitive processes.

Beyond wide tunability and long coherence length, other important parameters for tunable lasers for a variety of applications include tuning speed and variability of tuning speed. In SS-OCT, increased tuning speed enables imaging of time-varying physiological processes, as well as real-time volumetric imaging of larger data sets. Also for SS-OCT, variability of tuning speed enables switching between high speed, high resolution short-range imaging, and low speed, low resolution long range imaging in a single device, which is of great utility in, for example, ophthalmic imaging, as described in (Grulkowski, I., Liu, J. J., Potsaid, B. et al., "Retinal, anterior segment and full eye imaging using ultra-high speed swept source OCT with vertical-cavity surface emitting lasers," Biomed. Opt. Express, 3(11), 2733-2751 (2012)). Spectroscopic or other detection applications benefit in analogous ways from high-speed and variable speed.

Further desirable properties of widely tunable lasers include high output power, center wavelength flexibility, spectrally shaped output, monolithic and low-cost fabrication, and compatibility with array technology. High power increases signal to noise ratio for virtually every application. Center wavelength flexibility translates into greater utility in a larger variety of applications. Spectrally shaped output also increases signal to noise ratio and improves thermal management. Monolithic, low cost fabrication has obvious advantages, and array technology simplifies applications in which multiple sources are multiplexed.

The limitations of prior art tunable lasers with respect to the desirable properties above can be understood by examination of three representative examples. These examples include Fourier Domain mode-locked (FDML) lasers, external cavity tunable lasers (ECTL), and sampled grating distributed bragg reflector (SGDBR) lasers. An FDML laser is described in (Huber, R., Adler, D. C., and Fujimoto, J. G., "Buffered Fourier domain mode locking: unidirectional swept laser sources for optical coherence tomography imaging at 370,000 lines/s," Optics Letters, 31(20), 2975-2977 (2006)). Use of a commercial ECTL in an SSOCT system is described in (George, B., Potsaid, B., Baumann, B., Huang, D. et al., "Ultrahigh speed 1050 nm swept source/Fourier domain OCT retinal and anterior segment imaging at 100,000 to 400,000 axial scans per second," Optics Express, 18(19), 20029-20048 (2010)). Operation of an SGDBR laser is described in (Derickson, D., "High-Speed Concatenation of Frequency Ramps Using Sampled Grating Distributed Bragg Reflector Laser Diode Sources for OCT Resolution Enhancement," Proceedings of the SPIE—The International Society for Optical Engineering 7554, (2010)). FDML and ECTL devices are essentially multi-longitudinal mode devices, which sweep a cluster of modes instead of a single mode across a tuning range. This results in limited imaging range for SSOCT and limited spectral resolution for spectroscopic applications. Both FDML and ECTL are also non-monolithic sources, which are assembled from discrete components, and therefore not low cost devices or compatible with array fabrication. The ECTL further suffers from fundamental speed limitations of about 100 kHz repetition rate or less, due to the long time delay in the external cavity, as described in (Huber, R., Wojtkowski, M., Taira, K. et al., "Amplified, frequency swept lasers for frequency domain reflectometry and OCT imaging: design and scaling principles," Optics Express, 13(9), 3513-3528 (2005).) Further speed limitations in ECTL devices arise from the large mass of the grating tuning element, as for example in the commercially available Thorlabs model SL1325-P16 grating tuned laser. The FDML suffers also from inflexiblity of both center wavelength and tuning speed. Since the FDML employs a long fiber-based cavity, it can only operate at wavelengths where low-loss optical fiber is readily available. Secondly, the FDML sweep rate is fixed by the roundtrip time of light in the fiber external cavity, and variable sweep rates are therefore not possible in a single devices.

The SGDBR is a single transverse and longitudinal mode device, and has the potential for long imaging range and narrow spectral width. Tuning, however, is accomplished by discontinuous hopping amongst various modes, which tends to introduce measurement artifacts. The mode-hopping also requires multiple tuning electrodes, complicated drive circuitry and associated speed limitations. The SGDBR also suffers from limited tuning range relative to external cavity and FDML lasers, since the latter use lossless tuning mechanics, while the SGDBR is tuned by free carrier injection, which introduces free carrier losses and limits tuning range. The SGDBR also suffers from center wavelength inflexibility, due to the need for complex regrowth fabrication technology which is only mature in the Indium Phosphide material system.

The problems discussed above with respect to the FDML, ECTL, and SGDBR above are representative of problems encountered by most tunable lasers known in the art.

MEMS-tunable vertical cavity lasers (MEMS-VCSELs) offer a potential solution to the problems above. The short cavity of MEMS-VCSELs leads to a large longitudinal mode spacing and relative immunity to mode hops. The MEMS-VCSEL requires only one tuning electrode to sweep a single mode across the tuning range, and therefore offers the promise of long SS-OCT imaging range with minimal measurement artifacts, and rapid tuning. The short cavity and the short mass of the MEMS mirror offer the potential for very high speed. MEMS-VCSEL technology can also be extended to a large variety of wavelength ranges difficult to access with many other types of sources, making them appropriate for other types of spectroscopic, diagnostic, and detection systems. The application of MEMS-VCSELs to SS-OCT imaging was first described in U.S. Pat. No. 7,468,997. MEMS-VCSELs have the potential for wide tuning range, as discussed in U.S. Pat. No. 7,468,997. Until 2011, however, the widest MEMS-VCSEL tuning range achieved was 65 nm around 1550 nm, as described in (Matsui, Y., Vakhshoori, D., Peidong, W. et al., "Complete polarization mode control of long-wavelength tunable vertical-cavity surface-emitting lasers over 65-nm tuning, up to 14-mW output power," IEEE Journal of Quantum Electronics, 39(9), 1037-10481048 (2003). This represents a fractional tuning range of about 4.2%, or about a factor of 2 less than that required in SS-OCT imaging.) In 2011, a tuning range of 111 nm was demonstrated in a 1310 nm MEMS-VCSEL, which was subsequently applied in an SSOCT imaging system, as described in (Jayaraman, V., Jiang, J., Li, H. et al., "OCT Imaging up to 760 kHz Axial Scan Rate Using Single-Mode 1310 nm MEMS-Tunable VCSELs with >100 nm Tuning Range," CLEO: 2011—Laser Science to Photonic Applications, 2 pp.-2 pp.2 pp. (2011).)

The MEMS-VCSEL described by Jayaraman, et al. in 2011 represented a major innovation in widely tunable short cavity lasers. Achieving performance and reliability appropriate for commercial optical systems, however, requires optimization of tuning speed, frequency response of tuning, tuning range, spectral shape of tuning curve, output power vs. wavelength, post-amplified performance, gain and mirror designs, and overall cavity design. Numerous design innovations are required to improve upon the prior art to achieve performance and reliability necessary for these commercial systems.

From the foregoing, it is clear that what is required is a widely tunable short-cavity laser with 3-dimensional cavity and material design optimized for performance and reliability in SSOCT imaging systems, spectroscopic detection systems and other types of optical systems.

SUMMARY

This document provides several preferred embodiments of a tunable source comprising a short-cavity laser optimized for performance and reliability in SSOCT imaging systems, spectroscopic detection systems, and other types of detection and sensing systems. This document presents a short cavity laser with a large free spectral range cavity, fast tuning response and single transverse, longitudinal and polarization mode operation. The disclosure includes embodiments for fast and wide tuning, and optimized spectral shaping. Preferred embodiments include both electrical and optical pumping in a MEMS-VCSEL geometry with mirror and gain regions optimized for wide tuning, high output power, and a variety of preferred wavelength ranges. Other preferred embodiments include a semiconductor optical amplifier, combined with the short-cavity laser to produce high-power, spectrally shaped operation. Several preferred imaging and detection system embodiments make use of this tunable source for optimized operation.

One embodiment provides a tunable laser operative to emit tunable radiation over an emission wavelength range having a center wavelength, with an output power spectrum over said wavelength range and an average emission power, said tunable laser comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means for adjusting an optical path length has a wavelength tuning frequency response with a 6-dB bandwidth greater than about 1 kHz.

One embodiment provides an amplified tunable laser source, comprising input tunable radiation with an input power spectrum, an input center wavelength, input wavelength range and input average power, optically coupled to an input side of a semiconductor optical amplifier comprising at least one quantum well, and output tunable radiation having an output power spectrum, an output center wavelength, an output wavelength range, and output average power, emerging from an output side of said optical amplifier, wherein said input tunable radiation is generated by a tunable laser comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means for adjusting an optical path length has a wavelength tuning frequency response with a 6-dB bandwidth greater than about 1 kHz.

Another embodiment provides an amplified tunable laser source, comprising input tunable radiation with an input power spectrum, an input center wavelength, input wavelength range and input average power, optically coupled to an input side of a fiber-based optical amplifier comprising at least one quantum well, and output tunable radiation having an output power spectrum, an output center wavelength, an output wavelength range, and output average power, emerging from an output side of said optical amplifier, wherein said input tunable radiation is generated by a tunable laser comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means for adjusting an optical path length has a wavelength tuning frequency response with a 6-dB bandwidth greater than about 1 kHz.

One embodiment provides a tunable laser operative to emit tunable radiation over an emission wavelength range having a center wavelength, with an output power spectrum over said wavelength range and an average emission power, said tunable laser comprising: an optical cavity including a first and second mirror; a gain region interposed between said first and second mirrors; an airgap tuning region; and a MEMS-actuation mechanism for adjusting said airgap, said actuation mechanism comprising a deformable dielectric membrane transparent over said wavelength range and attached to a rigid support structure; wherein: a free spectral range (FSR) of said optical cavity exceeds 5% of said center wavelength; said tunable laser operates substantially in a single longitudinal and transverse mode over said wavelength range; and said MEMS-actuation mechanism has a wavelength tuning frequency response with a 6-dB bandwidth greater than about 1 kHz.

One embodiment provides a tunable laser operative to emit tunable radiation over an emission wavelength range having a center wavelength, with an output power spectrum over said wavelength range and an average emission power, said tunable laser comprising: an optical cavity including a first and second mirror; a quantum well gain region interposed between said first and second mirrors and comprising at least one quantum well; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; said means for adjusting an optical path length has a wavelength tuning frequency response with a 6-dB bandwidth greater than about 1 kHz, and each of said at least at least one quantum well is substantially aligned with a peak in an optical standing wave pattern of said optical cavity.

One embodiment provides a tunable laser operative to emit tunable radiation over an emission wavelength range having a center wavelength, with an output power spectrum over said wavelength range and an average emission power, said tunable laser comprising: an optical cavity including a first and second mirror; a gain region interposed between said first and second mirrors; a tuning region; means for adjusting an optical path length of said tuning region; and means to achieve a substantially single polarization state over said wavelength range; wherein: a free spectral range (FSR) of said optical cavity exceeds 5% of said center wavelength; said tunable laser operates substantially in a single longitudinal and transverse mode over said wavelength range; and said means for adjusting an optical path length has a wavelength tuning frequency response with a 6-dB bandwidth greater than about 1 kHz.

One embodiment provides an optical system for spectroscopic probing of a sample, said system comprising: a tunable laser; and means for detection; wherein said tunable laser is operative to emit tunable radiation over an emission wavelength range having a center wavelength, with an output power spectrum over said wavelength range and an average emission power, said tunable laser comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means for adjusting an optical path length has a wavelength tuning frequency response with a 6-dB bandwidth greater than about 1 kHz.

Another embodiment provides a system for optical beam steering, the system comprising: a tunable laser; and means to convert wavelength variation into beam deflection; wherein said tunable laser is operative to emit tunable radiation over an emission wavelength range having a center wavelength, with an output power spectrum over said wavelength range and an average emission power, said tunable laser comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means for adjusting an optical path length has a wavelength tuning frequency response with a 6-dB bandwidth greater than about 1 kHz.

Another embodiment provides a rapidly tuned oscillator, comprising: a tunable laser; a second laser; and means for generating a beat signal between radiation emerging from the tunable laser and radiation emerging from said second laser; wherein said tunable laser is operative to emit tunable radiation over an emission wavelength range having a center wavelength, with an output power spectrum over said wavelength range and an average emission power, said tunable laser comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means has a wavelength tuning frequency response with a 6-dB bandwidth greater than about 1 kHz.

Another embodiment provides an array of tunable lasers on a common wafer, wherein each of the tunable lasers is operative to emit tunable radiation over an emission wavelength range having a center wavelength, with an output power spectrum over said wavelength range and an average emission power, said each of the tunable lasers comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means for adjusting an optical path length has a wavelength tuning frequency response with a 6-dB bandwidth greater than about 1 kHz.

Another embodiment provides a high speed swept source comprising a tunable laser having a wavelength tuning range less than 50% of said FSR, and means for interleaving at least one copy of said wavelength sweep with the original sweep to generate a multiplied effective sweep rate; wherein the tunable laser is operative to emit tunable radiation over an emission wavelength range having a center wavelength, with an output power spectrum over said wavelength range and an average emission power, said tunable laser comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means has a wavelength tuning frequency response with a 6-dB bandwidth greater than about 1 kHz.

Another embodiment provides a high speed swept source comprising a first tunable laser and a second tunable laser, wherein each of the first and second tunable laser is operative to emit tunable radiation over an emission wavelength range having a center wavelength, with an output power spectrum over said wavelength range and an average emission power, said tunable laser comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means has a wavelength tuning frequency response with a 6-dB bandwidth greater than about 1 kHz; and wherein a first wavelength sweep of said first tunable laser and a second wavelength sweep of said second tunable laser are interleaved to generate a multiplied effective sweep rate.

Another embodiment provides a method for generating a desired output power variation vs. wavelength over a wavelength range from a tunable laser operative to emit tunable radiation over an emission wavelength range having a center wavelength, with an output power spectrum over said wavelength range and an average emission power, said tunable laser comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means for adjusting an optical path length has a wavelength tuning frequency response with a 6-dB bandwidth greater than about 1 kHz, the method comprising defining a target power variation over the wavelength range, and adjusting a reflectivity spectrum of one of said first and second mirrors until said output power variation matches said target power variation over the wavelength range.

Another embodiment provides a method for generating a desired output power variation vs. wavelength over a wavelength range from a tunable laser operative to emit tunable radiation over an emission wavelength range having a center wavelength, with an output power spectrum over said wavelength range and an average emission power, said tunable laser comprising: an optical cavity including a first and second mirror; a gain region interposed between said first and second mirrors; a tuning region; and means for adjusting an optical path length of said tuning region; wherein: a free spectral range (FSR) of said optical cavity exceeds 5% of said center wavelength; said tunable laser operates substantially in a single longitudinal and transverse mode over said wavelength range; and said means for adjusting an optical path length has a wavelength tuning frequency response with a 6-dB bandwidth greater than about 1 kHz, the method comprising shaping a pump energy entering into the gain region vs. wavelength to achieve a target output power variation vs. wavelength over the wavelength range.

DETAILED DESCRIPTION

Figure 1:
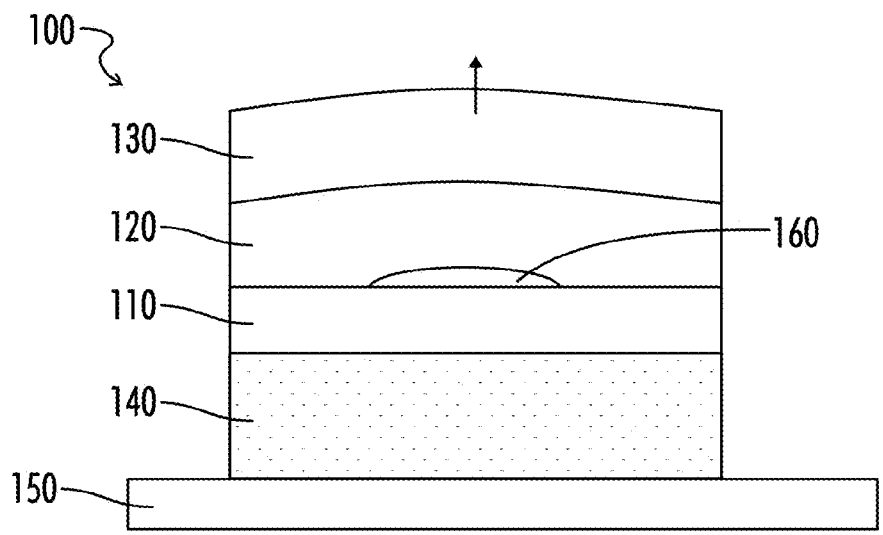
FIG. 1 illustrates an embodiment of widely tunable short cavity laser according to an embodiment.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

Figure 2:
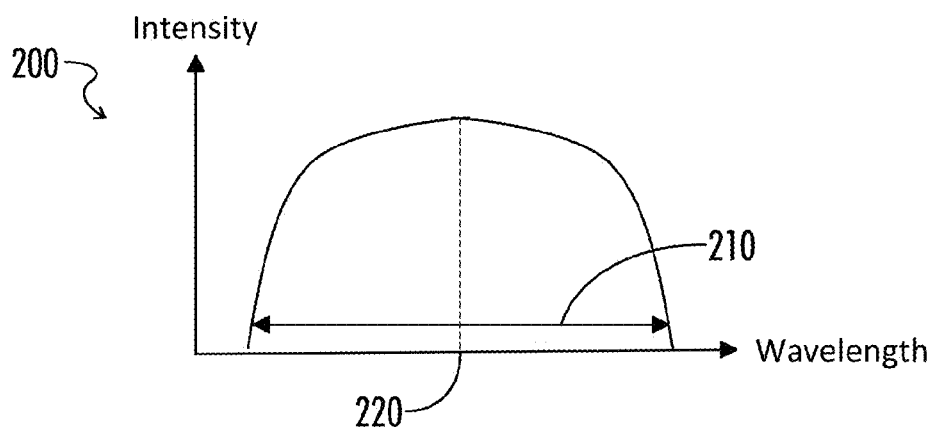
FIG. 2 illustrates an output power spectrum of a widely tunable short-cavity laser.
Figure 3:
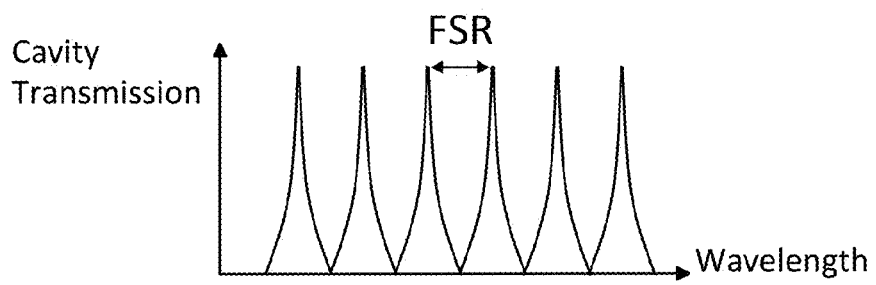
FIG. 3 illustrates the definition of free spectral range.

FIGS. 1-3 illustrate properties of a preferred embodiment of a short-cavity tunable laser in accordance with the present invention. As shown in FIG. 1, the laser 100 comprises a gain region 110 and a tuning region 120, interposed between a first mirror 130 and a second mirror 140. Energy to support lasing operation can be supplied to the gain region in the form of optical or electrical pumping, as is well-known to those skilled in the art of lasers. A thermally conductive heat spreading layer 150, preferably a metal such as gold, gold-tin, indium, or indium containing solder adjacent one mirror can also be employed to increase an average output power of the tunable short cavity laser. In the case of a vertical cavity laser on a GaAs substrate, for example, a substrate via could be etched, stopping on the second mirror, on which the heat-spreading layer could be deposited through the substrate via.

Referring to FIG. 1, adjustment of the effective optical path length of the tuning region causes the wavelength of the laser to be tuned. The laser emits wavelength tunable radiation, which is emitted through the first mirror. A typical emitted power spectrum 200, which is the power emitted as a function of wavelength, as shown in FIG. 2. The Spectrum represents range of wavelengths in tunable emission and intensity at each wavelength. The wavelength tunable emission spans a wavelength emission range 210 having a center wavelength 220. In the preferred embodiment of FIG. 1, the tuning region is an adjustable airgap, but other embodiments such as a liquid crystal or semiconductor whose optical path can be modified by adjustment of the refractive index are also possible.

A preferred embodiment of the short-cavity tunable laser of FIG. 1 is a vertical cavity laser (VCL), but other embodiments, including but not limited to short-cavity edge-emitting lasers, could be employed. As is well-known to those skilled in the art of vertical cavity lasers, the VCL can be fabricated in monolithic one and two-dimensional arrays, which is advantageous for optical systems requiring multiple optical sources. Modern wafer scale optical fabrication techniques would allow for the precise location of such an array of laser emitters, as well as optical components which would then support the manufacturing of optical instruments from these arrays.

The short cavity employed in an embodiment results in a large free-spectral range (FSR), which is inversely related to cavity length. The present embodiment discloses an FSR which in the present invention is >5% of the center wavelength shown in FIG. 2. As shown in FIG. 3, free spectral range is defined as the distance between transmission peaks, or longitudinal modes, in the direction of laser oscillation, of the optical cavity defined by the layers of FIG. 1. The maximum continuous mode-hop-free single-mode tuning range of the tunable laser is limited by the FSR. Thus, a laser having an FSR that is 5% of the center wavelength can be expected to have a maximum tuning range that is 5% of the center wavelength. Other considerations, such as the maximum achievable change in optical path length of the tuning region, or the available gain bandwidth of the gain region may limit the continuous single mode tuning range to less than the FSR, but the FSR represents an upper limit.

In the preferred embodiment, an anti-reflection coating is placed between the gain region and the tuning region to suppress reflections in the device and extend the tuning range. This anti-reflection coating can be a quarter wavelength of material such as silicon nitride or silicon oxynitride, in the preferred case when the tuning region is air, and the gain region is semiconductor.

FIG. 1 also illustrates that the top mirror 130 can be curved to form a half-symmetric cavity as in (Tayebati, P., Wang, P., Vakhshoori, D. et al., "Half-symmetric cavity tunable microelectromechanical VCSEL with single spatial mode," IEEE Photonics Technology Letters, 10(12), 1679-1681 (1998)), which includes one curved mirror and one flat mirror. This is important because, although the short cavity and large FSR promote single longitudinal operation, the curved mirror further promotes single transverse mode operation, which is important for applications in imaging and spectroscopy. The function of the curved mirror can also be accomplished by an intra-cavity microlens 160, as shown in FIG. 1. Generally either the microlens 160 or the curved mirror 130 can be used, but a combination of both can also be used. The microlens can be formed by reflow of a resist or polymer material, followed by pattern transfer of that shape into underlying materials, as is described in (Strzelecka, E. M., Robinson, G. D., Coldren, L. A. et al., "Fabrication of refractive microlenses in semiconductors by mask shape transfer in reactive ion etching," Microelectronic Engineering 35(1-4), 385-388 (1997)) and known to those who are skilled in the art. Similarly, the curved mirror can be formed by structuring of sacrificial layer by a reflow and pattern transfer technique, deposition of the top mirror, and removal of the sacrificial layer. The sacrificial layer in such a process is preferably silicon or germanium, and the pattern transfer of a reflowed resist layer can be accomplished by inductively coupled plasma etching using a CF4/oxygen gas mixture. The curvature of the resulting surface in the sacrificial layer is a function of the ratio of these gases, and can be adjusted by straightforward optimization of this ratio.

Achieving single transverse-mode operation of the tunable short cavity laser in FIG. 1 requires careful control of the curved mirror radius of curvature and the combined thickness of gain region and tuning region between the two mirrors. For the case of an airgap tuning region and operation near 1310 nm using a semiconductor gain region comprised of InP-based materials, typical dimension are a gain region thickness of about 1 micron, airgap thickness of about 1.6 µm, and a mirror radius of curvature of around 1 mm. Those skilled in the art of laser fabrication and design can adjust numbers in this range to achieve more specific numbers for particular designs in particular wavelength regimes. Using parameters close to these will lead to single longitudinal and transverse mode suppression of 40-50 dB.

Figure 5:
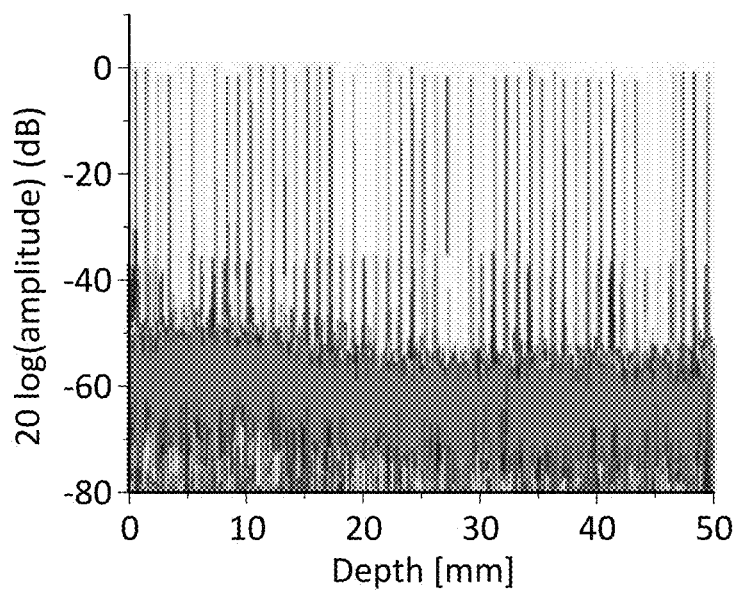
FIG. 5 shows a measurement dynamic coherence length obtained by the rolloff of the OCT point spread function vs. imaging depth.

The single longitudinal and transverse mode operation achieved by the short cavity laser according to an embodiment enables an optical source with very long dynamic coherence length. This coherence length is in excess of 100 mm under dynamic operation. Coherence length is inversely related to laser line-width. Long coherence length is important in spectroscopic applications requiring the measurement of narrow spectral features. In imaging applications like swept source optical coherence tomography (SS-OCT), long coherence length corresponds to long imaging range. FIG. 5 shows a detection-limited measurement of coherence length in an SS-OCT system, obtained by repetitive sweeping at 60 kHz of a tunable laser according to FIG. 1, in which the FSR is about 8-9% of the center wavelength, and using the OCT point spread function as a measurement of coherence length. The absence of substantial amplitude degradation at 50 mm indicates that the coherent length is greater than 100 mm. This measurement method is well-known to those skilled in the art of SS-OCT.

For some applications, it is advantageous to reduce the coherence length to eliminate interference from unwanted reflections in an optical system. Coherence length can be adjusted by adding a noise waveform to the tuning region, or otherwise amplitude or phase modulating the source. External means could include, for example, a temporal diffuser.

In an embodiment, the frequency response of the optical path length of a tuning region to an applied tuning signal has a 6-dB bandwidth that exceeds about 1 kHz. Normally, this 6-dB bandwidth starts at DC but can start at some non-zero frequency as well. The 1 kHz bandwidth distinguishes the present invention from other types of tuning mechanisms employed in the prior art, such as electro-thermal tuning in (Gierl, C., Gruendl, T., Debernardi, P. et al., "Surface micromachined tunable 1.55 mu m-VCSEL with 102 nm continuous single-mode tuning," Optics Express, 19(18), 17336-17343 (2011)). In the preferred case where the tuning region is an airgap, the airgap can be tuned by a MEMS-based actuator, which contracts the airgap through electrostatic force. MEMS-based tuning mechanisms have been demonstrated to have a 6-dB bandwidth exceeding 500 kHz, as illustrated in (Jayaraman, V., Cole, G. D., Robertson, M. et al., "High-sweep-rate 1310 nm MEMS-VCSEL with 150 nm continuous tuning range," Electronics Letters, 48(14), 867-9 (2012)). As described below, the bandwidth of a MEMS-actuator can be extended to >1 MHz. The presence of such a wide bandwidth enables repetitively swept operation at a range of frequencies from DC to >1 MHz. It also enables non-repetitive wavelength tuning at a variety of scan speeds. The ability to vary the fundamental tuning frequency of the laser within one laser source makes the instrument appropriate for a broad range of applications, each of which have a preferred tuning rate. For example, the measurement of weak spectroscopic signals could require slow scanning speeds, whereas strong spectroscopic signals could be monitored such that dynamic temporal effects could be captured. Many applications in SSOCT could also benefit from variable scan frequency, which enables tradeoff of imaging resolution and imaging range with imaging speed.

Figure 11:
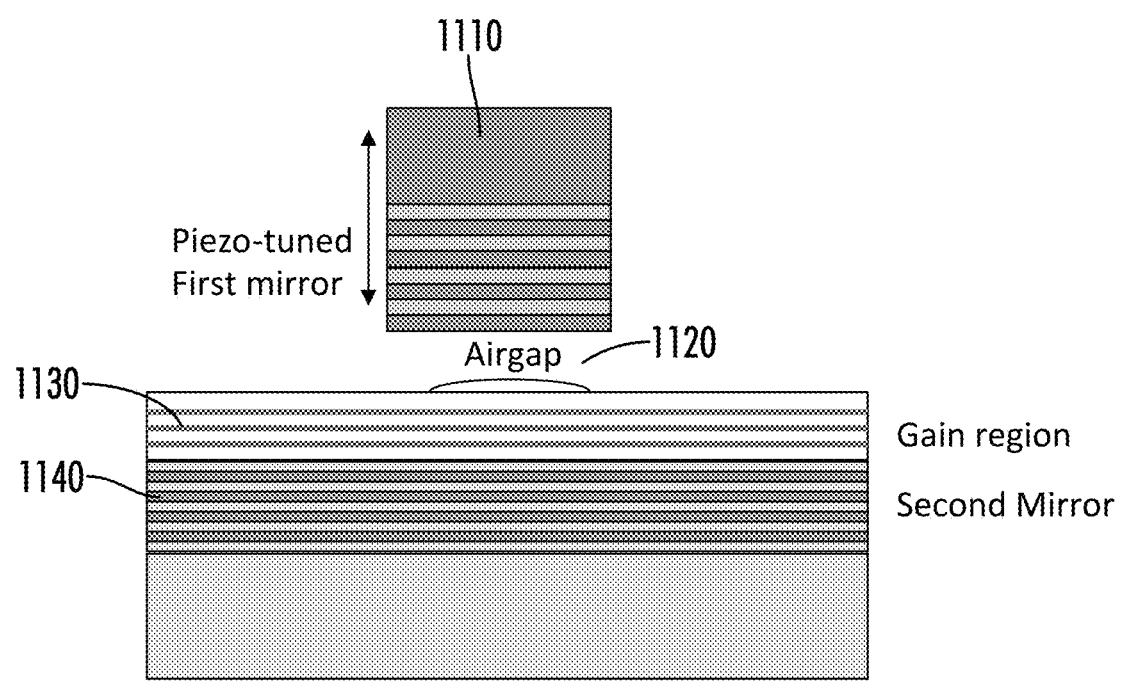
FIG. 11 illustrates a widely tunable short-cavity laser with piezo tuning.

Although MEMS tuning of an airgap is the preferred embodiment of the present invention, an alternative embodiment could tune the airgap through a piezo-electric actuator, such as described by (U.S. Pat. No. 6,263,002). This configuration is illustrated also in FIG. 11, where the top mirror 1110 is placed on a piezo-electric actuator and separated by an airgap 1120 from the gain region 1130 and the bottom mirror 1140. The first mirror 1110 is moved relative to the gain region 1130 via piezo-electric control changing the airgap 1120 tuning region and therefore, the lasing wavelength. In this structure, the first mirror is attached to a fiber that can deliver pump radiation and collect laser radiation. Piezo tuning can also provide several kHz of bandwidth, which is generally less than the bandwidth of MEMS tuning, but piezo tuning can produce larger airgap changes, and can be bi-directional. It is also possible to obtain bi-directional tuning in a MEMS device through a 3-terminal device. In yet another embodiment, piezo and MEMS tuning can both be used to provide a combination of a slower, large stroke tuning mechanism, and a faster, small stroke tuning mechanism. These tuning mechanisms can be combined further with other tuning mechanisms such as carrier injection tuning in semiconductors.

The tuning region can be driven with a variety of waveforms, to generate various wavelength trajectories vs. time out of the short-cavity laser for a variety of applications. For example, the tuning region can be driven with a repetitive waveform having a fundamental frequency, generating a periodic variation of wavelength vs. time for applications such as swept source optical coherence tomography (SSOCT). The periodic waveform could be sinusoidal in shape, or an arbitrary waveform constructed to generate a linearized wavelength sweep vs. time or any wavelength trajectory with time. The response of the tuning region may be non-linear with respect to the applied waveform. A classic example is MEMS, in which the movement of an electrostatically actuated membrane varies as the square of applied voltage. In this case, creating a linear movement requires pre-distorting the applied waveform to account for the non-linear response of the MEMS actuator. The generation of arbitrary waveforms to linearize MEMS response is well-known to those skilled in the art of driving MEMS devices, but the principle of linearization can be applied to other tuning mechanisms as well.

The waveform applied to the tuning region is usually a variation in applied voltage or current vs. time, depending on the exact nature of the tuning region and mechanism of tuning, whether it be changing a physical path length or changing a refractive index of a semiconductor or liquid crystal, as some representative examples. By way of example, use of a MEMS based tuning element with its very low mass reduces the power required to sweep the laser wavelength in both a continuous sweep as well as in a non-continuous sweep. The use of a MEMS tuning element would require a drive voltage with very little current drawn.

In addition to repetitive wavelength sweeping, the tuning region can be driven by a non-repetitive waveform, in response to an external trigger, or by any repetitive or non-repetitive arbitrary waveform. Examples of this are in transient spectroscopy, where it is advantageous to measure the transmission, absorption, or reflection spectrum of a material shortly after an event, such as an explosion, chemical reaction, or a biological event. Non-repetitive scanning would also facilitate new modes of operation whereby a number of narrow regions of interest separated by large regions of no interest could be interrogated with the laser in an optimized manner. One example is a series of slow scans across narrow spectroscopic features that are separated by large regions wherein the large regions are scanned at high speed. In the preferred case of MEMS tuning, many new operating modes are made possible by the extremely low mass of the tuning element that allows for rapid acceleration and deceleration of the laser tuning speed.

With respect to scanning in response to an external trigger, the advantages of a MEMS implementation of the present invention are illuminated by a comparison with the commercially available Thorlabs model SL1325-P16 swept source laser (which is not a short-cavity laser). This prior art laser utilizes a resonantly scanned optical grating measuring over 10 mm$^2$ as the tuning element, causing slow response time relative to a low mass MEMS element in the present invention. In an embodiment according to the present invention the very low mass of the tuning element allows greater flexibility in the operating parameters, such as how quickly the laser can respond to an external event, as well as the wavelength region over which the laser is tuned as a result of an external event. This flexibility provides new modes of operation when it is desirable to synchronize the operation of the laser with external events.

Having the laser tune across a widely adaptable tuning profile allows the performance of the laser to be adjusted to meet the demands of many applications. By way of example, in one application it would be desirable to scan the wavelength of the laser linearly in time if the laser is being used to measure the wavelength dependence of an optical element, in other applications would be desirable to scan the laser linearly in optical frequency when the laser is being employed to make measurements that are best made with samples equally spaced in frequency, such as is the case in Optical Coherence Tomography.

Figure 4:
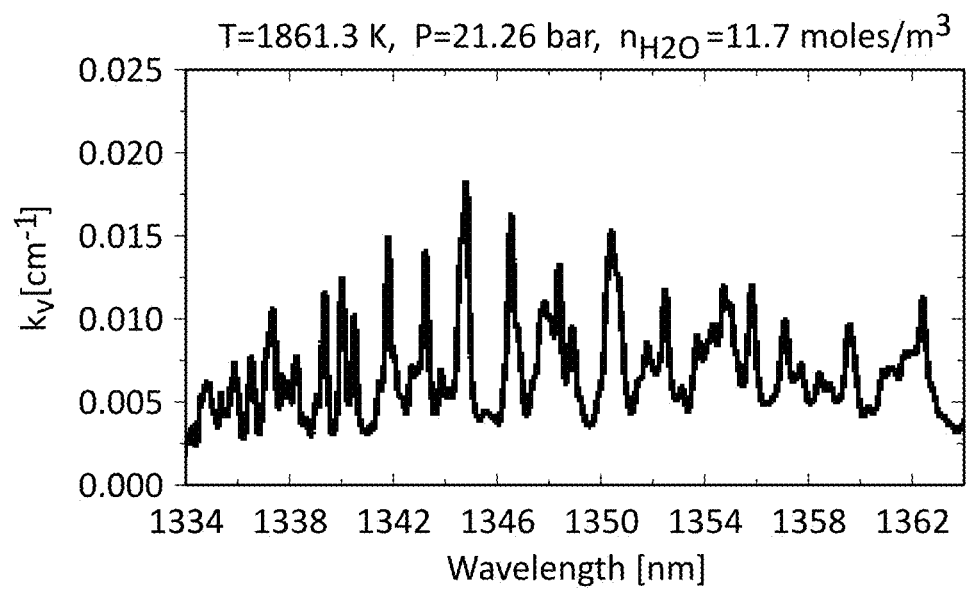
FIG. 4 shows a water vapor absorption spectrum in the 1330-1365 nm rang.

Spectroscopy provides another example of the utility of a highly flexible tuning profile. In many spectroscopic applications, it is necessary to measure multiple unequally spaced and variable linewidth lines across a range of wavelengths. Maximizing overall signal to noise ratio requires slower scan speeds in information rich (e.g. many narrow lines) regions of the spectrum and faster scan speeds in regions of the spectrum with less or no information. FIG. 4 shows an example of a water vapor absorption spectrum in the 1330-1365 nm range.

For many applications, such as those described above, the tuning region of the tunable short-cavity laser according the present region can be driven open loop—that is, without position or wavelength feedback. In other applications where wavelength stability is more important, however, feedback control can be employed. This can be advantageous in static operation, when the wavelength is locked to a particular atomic absorption line or other atomic reference. Alternately, the wavelength can be first locked to an atomic reference and then offset from this reference using another element to measure the offset distance, such as a Fabry-Perot or Mach-Zehnder interferometer having a known fringe spacing. Closed loop control can also be advantageous in dynamic operation.

Figure 6:
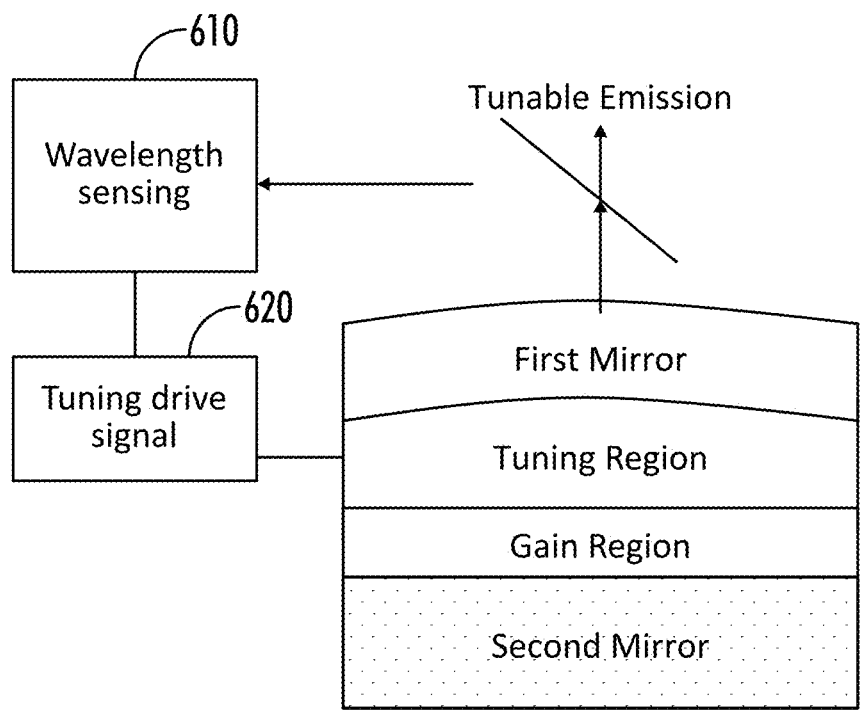
FIG. 6 illustrates an embodiment of a widely tunable short-cavity laser with closed loop control.

FIG. 6 shows a preferred embodiment of closed loop control according to the present invention. As shown, a portion of the light emitted from the tunable short-cavity laser is split to a wavelength-sensing element 610, which can comprise elements such as a prism, grating, optical filter, or optical interferometer. In the case of a dispersive element like a prism or a grating, a position-sensing element like a detector array would be combined with the dispersive element to detect diffracted or refracted angle and infer wavelength offset from the desired position and feed this error signal to the tuning drive waveform 620. If the application doesn't require a specific wavelength but just that a fixed wavelength, or a series of fixed wavelengths be delivered, then the wavelength dispersing element and the position sensing element could be used without calibration of the dispersing element. In the case of an optical filter, the transmission or reflection of the filter as measured by an optical detector would be used to determine wavelength offset from a desired lock position and feed an error signal back to the tuning region drive waveform. Dynamic closed loop operation can be obtained by scanning the error signal, as has been shown in prior art lasers, such as FIG. 1 of (Roos, P. A., Reibel, R. R., Berg, T. et al., "Ultrabroadband optical chirp linearization for precision metrology applications," Optics Letters, 34(23), 3692-3694 (2009).) Closed loop control is particularly useful when driving a tuning region at speeds well below a natural resonance, which may create variabilities. For example, a MEMS actuator with a 500 kHz resonance driven at 100 kHz may be prone to variability and may have much more well-behaved tuning with closed loop control.

Figure 7:
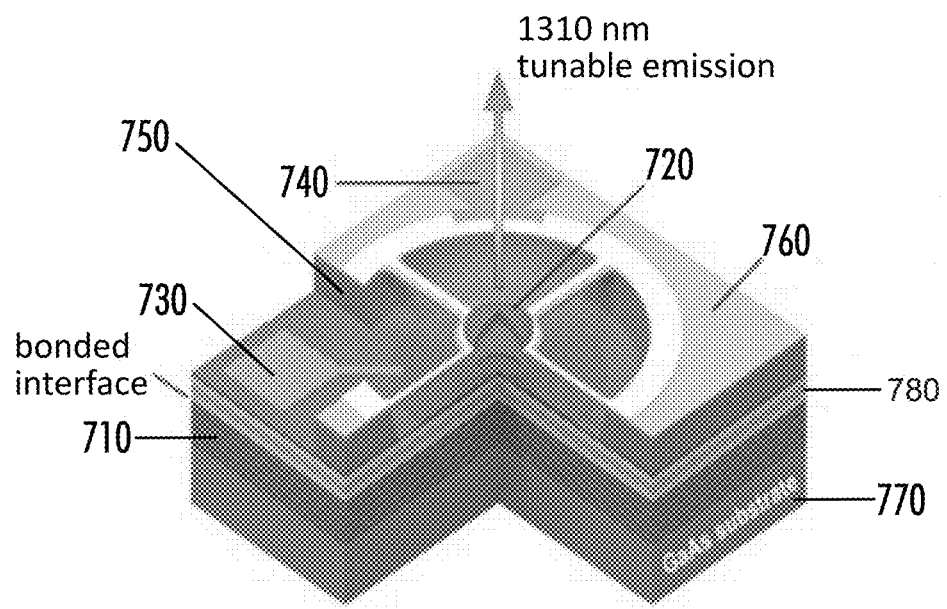
FIG. 7 illustrates a MEMS-VCSEL implementation of a tunable short cavity laser operating near 1310 nm.
Figure 9:
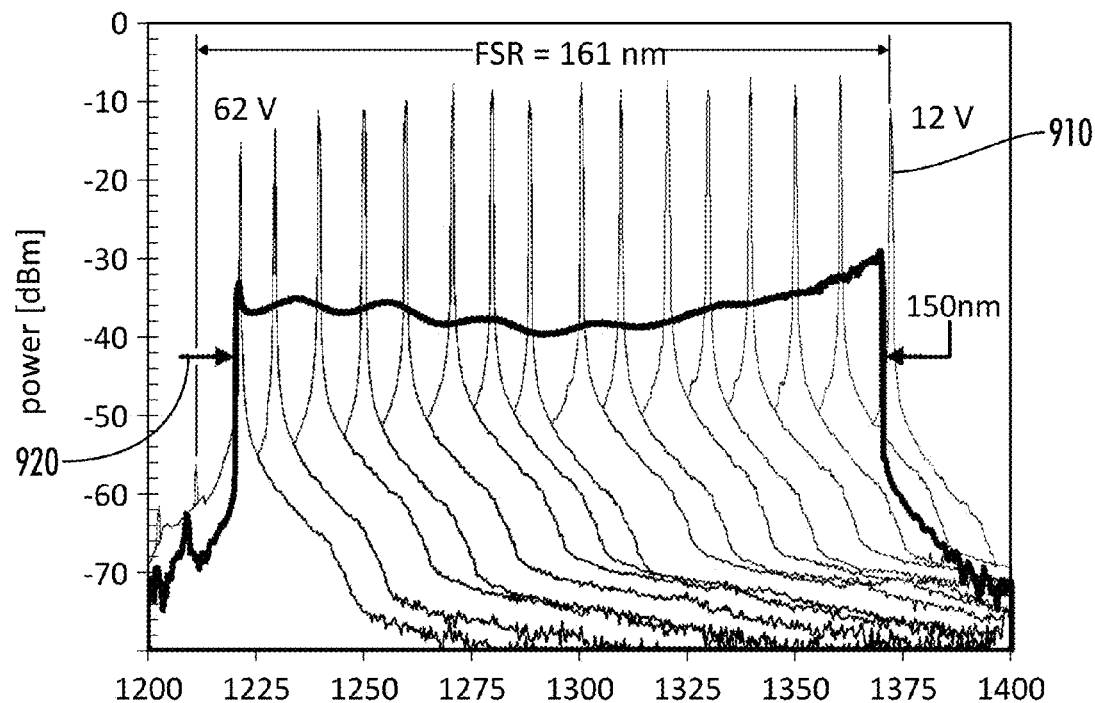
FIG. 9 illustrates the static and dynamic tuning response of the MEMS-VCSEL illustrated in FIG. 7.
Figure 10:
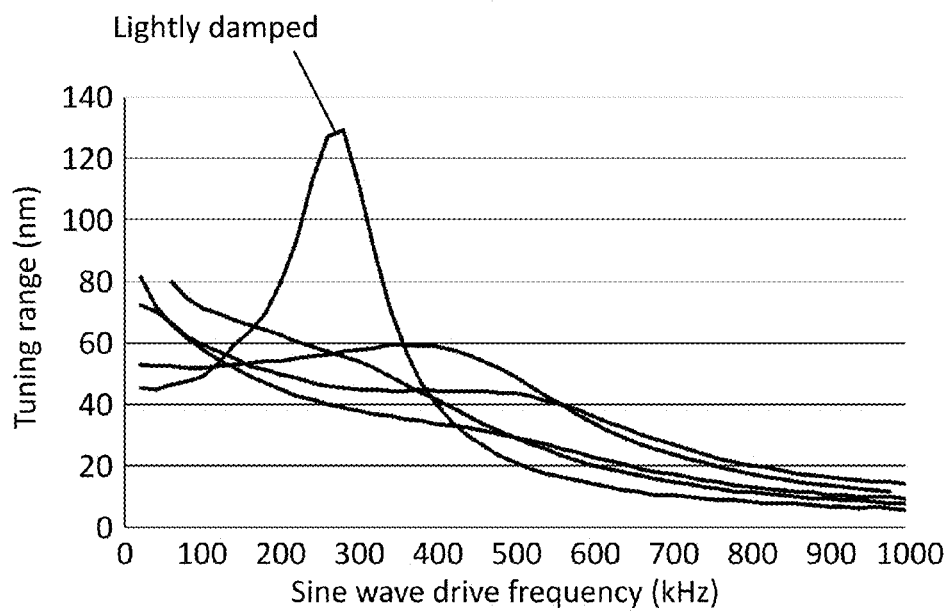
FIG. 10 illustrates a variety of MEMS-VCSEL actuator frequency responses.

FIG. 7 illustrates several details of a preferred implementation of a short-cavity laser constructed to operate at 1310 nm according to an embodiment of the present invention, and FIGS. 9 and 10 demonstrate several additional performance features of the implementation of FIG. 7. FIG. 7 illustrates a semiconductor laser constructed as a vertical cavity surface emitting laser (VCSEL), which is a subset of vertical cavity lasers (VCL). A VCL can emit either downward or upward, and VCSELs emit upward, meaning in the direction opposite the substrate. The VCSEL of FIG. 7 employs two distributed Bragg reflector (DBR) mirrors 710, 720 comprising alternating quarter wave layers of low and high refractive index material. The DBR is preferred for both mirrors, although a high contrast grating as used by prior art lasers can also be employed, as described in for example (Chase, C., Rao, Y., Hofmann, W. et al., "1550 nm high contrast grating VCSEL," Optics Express, 18(15), 15461-15466 (2010)).

The bottom mirror 710 of FIG. 7, corresponding to the second mirror 140 of FIG. 1, is comprised of alternating quarter wave layers of GaAs and Aluminum oxide (AlxOy). This type of mirror is formed by lateral oxidation of an epitaxially grown stack of GaAs/AlAs, as described in (MacDougal, M. H., Dapkus, P. D., Bond, A. E. et al., "Design and fabrication of VCSELs with AlxOy—GaAs DBRs," IEEE Journal of Selected Topics in Quantum Electronics, 3(3), 905-915915 (1997)). The GaAs/AlxOy mirror has a large reflectivity and wide bandwidth with a small number of mirror periods. The preferred number of mirror periods for the back mirror, when light is coupled out the top mirror as in FIG. 7, is six or seven periods, creating a theoretical lossless reflectivity of >99.9%. Other implementations of this mirror could use AlGaAs/AlxOy, where the aluminum content of the AlGaAs is less than about 92%, so that it does not oxidize appreciably during lateral oxidation of the AlAs to form AlxOy. Use of AlGaAs instead of GaAs for the low index material is advantageous for increasing the bandgap of the low-index material to make it non-absorbing at the lasing wavelength or at the pump wavelength if the laser is optically pumped.

The top suspended mirror 720 of FIG. 7, corresponding to the first mirror 130 of FIG. 1, is comprised of alternating low and high refractive index deposited materials, such as for example $SiO_2$ and $Ta_2O_5$. Other deposited materials could be used as well, including but not limited to the list consisting of $TiO_2$, $HfO_2$, Si, Ag, Al, Au, ZnS, ZnSe, $CdF_2$, $Al_2F_3$, and CdS. These materials can be deposited by electron beam evaporation, ion beam sputtering, plasma-assisted deposition, or other means well-known to those skilled in the art. For the example, in case of a 10 period $SiO2/Ta_2O_5$ period mirror having refractive indices of 1.46/2.07 respectively, centered in a range of about 700 nm to about 1600 nm, the theoretical lossless reflectivity exceeds 99.5% over a range of at least 10% of the center wavelength, as can be calculated by those skilled in the art of mirror design.

The implementation of FIG. 7 uses MEMS actuation to control the thickness of an airgap tuning region to control the output wavelength of the device in the range of 1310 nm. Application of a voltage between the actuator contacts 730, 740 shown contracts the airgap and tunes the laser to shorter wavelengths. The MEMS structure shown consists of a rigid supporting structure 750 and a suspended deformable dielectric membrane 760, on which is the suspended top mirror 720. The top of the dielectric membrane 760 is metallized to enable electrostatic force to be applied by the actuator contacts 730, 740. The membrane itself is transparent, runs underneath and is integral with the suspended mirror, and contributes constructively to the reflectivity of the suspended mirror. Ideally the membrane thickness is an odd number of quarter wavelengths at the center wavelength of the emitted tuned radiation. For many wavelengths of interest, such as in the 600-2500 nm range, the ideal thickness is about ¾ wavelength.

In the preferred embodiment, the dielectric membrane is silicon nitride, which is a robust material, which can be stress-engineered to create the desired frequency response. Ideally the silicon nitride has a tensile stress in the range or about 100 to about 1000 MPa. This range of stress leads to a lowest order resonant frequency of the MEMS actuator, described below, that is substantially increased by the stress. Although tensile stress is preferred, compressive can also be employed, though it is less preferred, since it leads to bowing of the membrane after MEMS release. Other authors have made advantageous use of this bowing to create a half-symmetric cavity, as described for example in (Matsui, Y., Vakhshoori, D., Peidong, W. et al., "Complete polarization mode control of long-wavelength tunable vertical-cavity surface-emitting lasers over 65-nm tuning, up to 14-mW output power," IEEE Journal of Quantum Electronics, 39(9), 1037-10481048 (2003)).

The representative preferred embodiment is shown in FIG. 7 is configured to operate at 1310 nm. This configuration therefore uses an InP-based multi-quantum well (MQW) region comprising at least one quantum well in the gain region. Since the bottom fully oxidized $GaAs/Al_xO_y$ mirror is grown on GaAs instead of InP, the InP-based MQW region must be joined to the GaAs-based fully oxidized mirror through a wafer bonding process, as described in fixed wavelength 1310 nm VCSELs such as in (Jayaraman, V., Mehta, M., Jackson, A. W. et al., "High-power 1320-nm wafer-bonded VCSELs with tunnel junctions," IEEE Photonics Technology Letters, 15(11), 1495-14971497 (2003)). The multi-quantum well region is preferably comprised of multiple compressively strained AlInGaAs quantum wells, with strain in a range of 1-1.5%. In another embodiment, it is possible to use a GaInNAs quantum well that can emit around 1310 nm and can be grown on GaAs, eliminating the need for wafer bonding. The AlInGaAs quantum well is however higher gain and more wavelength flexible, and is therefore preferred.

Figure 25:
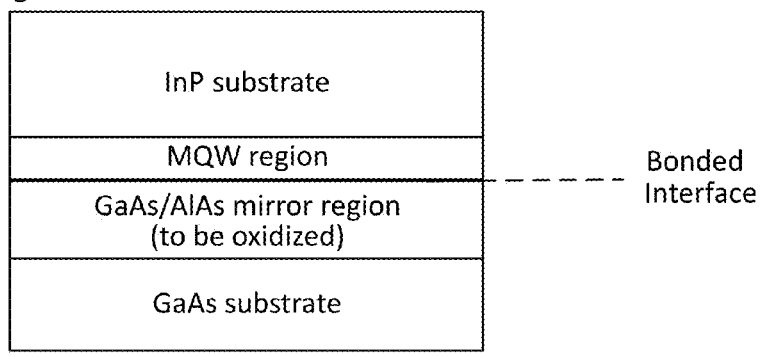
FIG. 25 illustrates steps 1-4 in the fabrication of a widely tunable short cavity laser realized as a MEMS-VCSEL.
Figure 25:
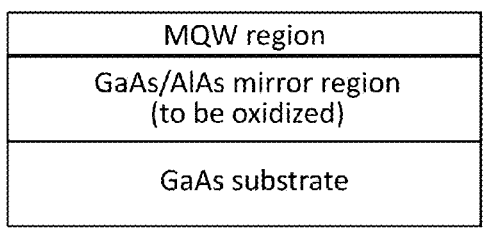
Figure 25:
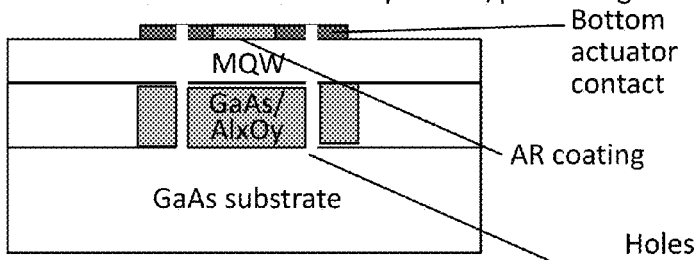
Figure 25:
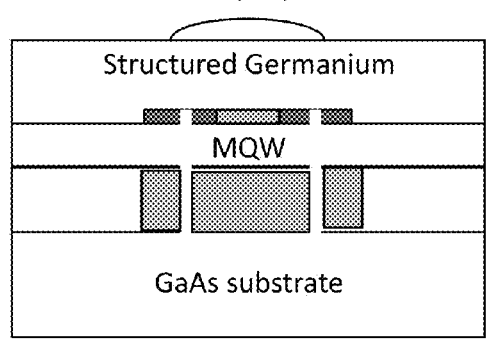
Figure 26:
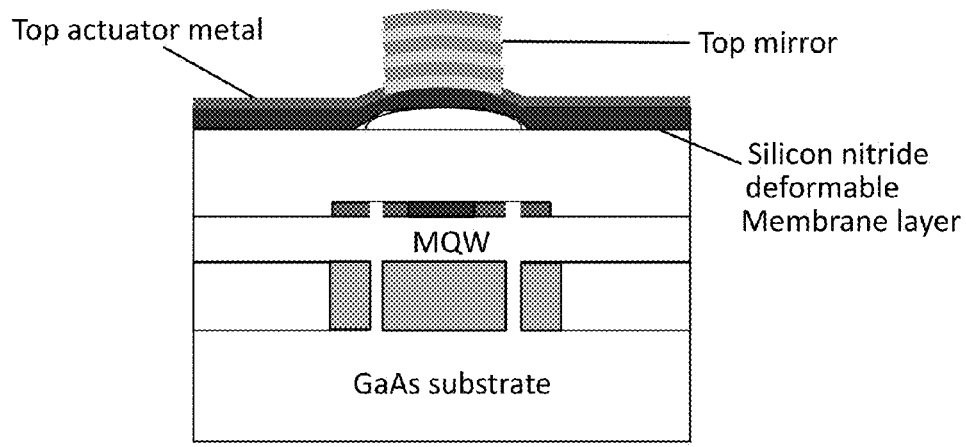
FIG. 26 illustrates steps 5-6 in the fabrication of a widely tunable short cavity laser realized as a MEMS-VCSEL.
Figure 26:
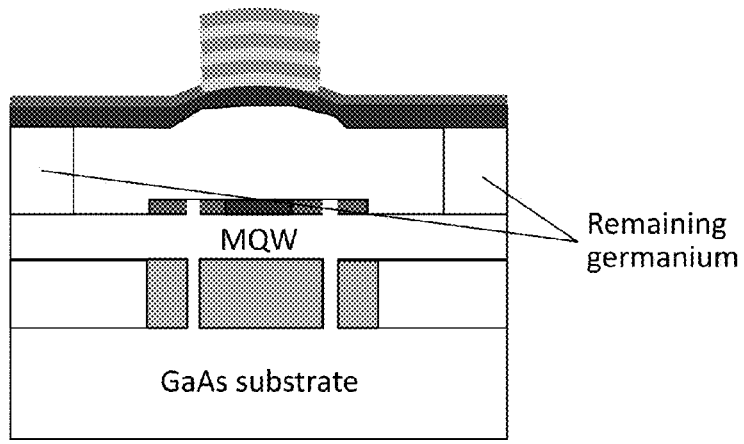

FIGS. 25 and 26 illustrate the major steps of a fabrication sequence used to fabricate the preferred implementation of the 1310 nm tunable short cavity laser in FIG. 7. Processing of devices in a wavelength range of 650-2300 nm can proceed in a similar fashion, with the except that GaAs-based devices do not require the first wafer bonding step shown in FIG. 25, since mirror and gain region can be epitaxially grown in one step. As shown in FIG. 25, at 1310 nm, or at any wavelength employing an active region grown on InP, the first step 2510 involves wafer bonding of the MQW region epitaxially grown on an InP substrate to a GaAs/AlAs mirror structure epitaxially grown on a GaAs substrate. This process can be accomplished through the application of pressure and about 570 C temperature for about 15 minutes, as has been described in greater detail by prior art researchers in (Black, A., Hawkins, A. R., Margalit, N. M. et al., "Wafer fusion: Materials issues and device results," IEEE Journal of Selected Topics in Quantum Electronics, 3(3), 943-951 (1997)). The MQW and the mirror structure are joined at a wafer-bonded interface. After bonding, the InP substrate is removed in a second step 2520 using an HCL-based etch stopping on an InGaAs stop etch layer. A sulfuric acid based etch then removes the stop-etch layer.

In a third series of steps 2530, the bottom MEMS contact, which is preferably terminated with titanium to promote adhesion of germanium in a subsequent step, and anti-reflection coating are deposited and patterned, and holes are etched for oxidation of the GaAs/AlAs mirror structure. Oxidation converts the AlAs to $Al_xO_y$ to create a highly reflecting mirror with six or seven periods. After mirror oxidation, a germanium sacrificial layer is deposited in a fourth step 2540, and the germanium is structured to have a curved surface in the region of light oscillation. This curved surface is created by a photoresist reflow and pattern transfer process, using an oxygen-rich $CF_4/O_2$ inductively coupled plasma etch process. FIG. 26 illustrates how in a $5^{th}$ series of steps 2550, the silicon nitride membrane layer, top actuator contact, and top suspended mirror are deposited and patterned on the germanium sacrificial layer. The top contact layer is preferably aluminum.

In a $6^{th}$ series of steps 2560, the germanium sacrificial layer is released using Xenon Diflouride ($XeF_2$) gas to create a suspended structure with a rigid germanium support structure at the edges. Prior to the germanium release, wire bond pads, shown in FIG. 7 connecting with the top and bottom actuator metal, are deposited to complete processing before release. Processing after release is generally not advisable, as it can lead to collapse of the actuator. In many cases, it is preferable to dice and wire bond devices to a submount for packaging, prior to releasing the germanium membrane.

The design of the gain region in the preferred embodiment of FIG. 7 is important for device performance. In the case where the structure is optically pumped, the quantum wells can be aligned with peaks of an optical standing wave to enhance gain through the well-known periodic gain effect, described in the prior art by (Corzine, S. W., Geels, R. S., Scott, J. W. et al., "DESIGN OF FABRY-PEROT SURFACE-EMITTING LASERS WITH A PERIODIC GAIN STRUCTURE," IEEE Journal of Quantum Electronics, 25(6), 1513-1524 (1989)). One further advantage of periodic gain is that the wide spacing between quantum wells prevents strain accumulation and reduces the need for strain compensation. The ideal pump wavelength for the 1310 nm tunable VCSEL shown is in a range of about 850-1050 nm. In an optically pumped structure, three quantum wells can be placed on three separated standing wave peaks, and the region between them can be made of AlInGaAs substantially lattice-matched to InP, and of a composition that absorbs incoming pump radiation. Thus the gain region is separated from the absorbing regions, and photo-generated carriers in the absorbing regions diffuse into gain region. Alternately, the FSR of the structure can be increased by placing three quantum wells at a single standing wave peak. In this case, strain compensation of the compressively strained AlIn-GaAs wells with tensilely strained AlInGaAs may be required. This creates a thinner absorbing region, since absorption may occur only in the quantum wells. Such a structure will require more pump power in an optically pumped device, but will provide wider tuning range. One implementation of FIG. 7 using three quantum wells on a single standing wave peak enabled a structure with 161 nm FSR near 1310 nm, representing 12.3% of the center wavelength, as shown in the tuning results of FIG. 9. Continuous single-mode tuning range with this device was 150 nm, as also shown in FIG. 9 and discussed more below. FIG. 9 shows the static and dynamic tuning response of an ultra-widely tunable MEMS-VCSELs. The long-wavelength spectrum 910 at 1372 nm exhibits a completing mode at 1211 nm, illustrating the 161 nm FSR of the cavity. The curve 920 represents the time-averaged spectrum under sinusoidal sweeping at 500 kHz. Both the static and dynamic response demonstrate continuous single-transverse and longitudinal mode lasing operation over a 150 nm span. FSR in the range of 140-170 nm for 1310 nm devices provides device tuning that is exceptionally well suited for swept source optical coherence tomography systems. A large FSR is desirable not only as a means to increase the tuning range of the laser but also as a means to reduce the duty factor of the laser such that additional tuning profiles from other tunable short-cavity lasers can be added as described later. For example, if the gain bandwidth of the laser is restricted to <50% of the FSR, and the entire FSR is swept, then the laser automatically turns off for more than half the sweep, leaving room to interleave a sweep from another laser, or a time-delayed copy of the sweep, as described in for example (Klein, T., Wieser, W., Eigenwillig, C. M. et al., "Megahertz OCT for ultrawide-field retinal imaging with a 1050 nm Fourier domain mode locked laser," Optics Express, 19(4), 3044-30623062 (2011)).

Figure 8:
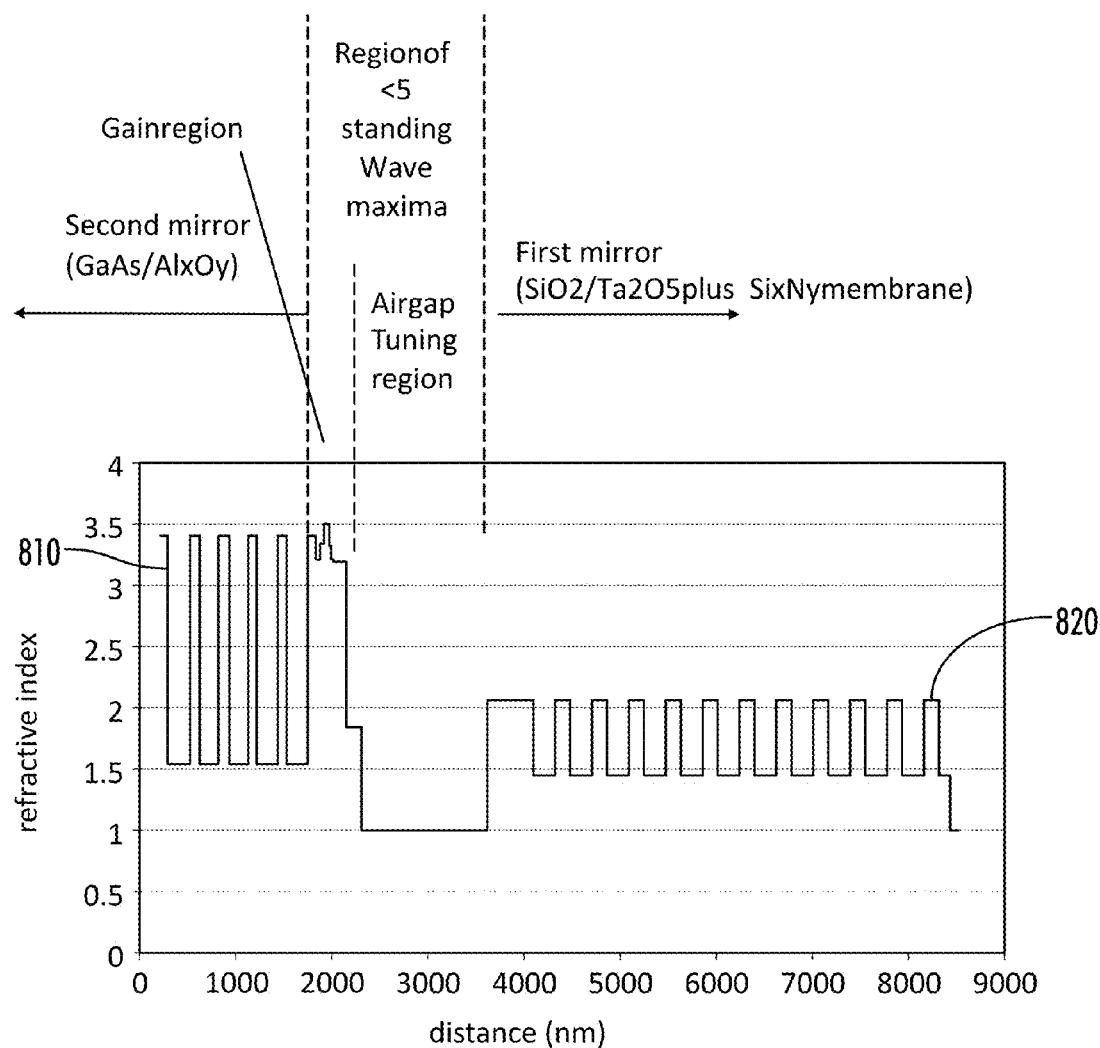
FIG. 8 illustrates an axial refractive index profile of a short cavity laser having 4 standing wave maxima between two mirrors of the cavity.

When it is desirable to maintain lasing over a very wide tuning range (>10% of center wavelength), it is advantageous to broaden the gain of the quantum wells by including a second confined quantum state in the well by using wider quantum wells as described in (U.S. Pat. No. 7,671,997). We note that the wide FSR structure producing the results of FIG. 9 employed can be characterized by the number of maxima in the optical standing wave formed between the mirrors during lasing operation. The results of FIG. 9 were produced by a structure with five standing wave maxima in the cavity between the bottom mirror and the suspended mirror. Further reduction of cavity thickness to below five standing wave maxima can lead to larger FSR approaching 200 nm for a 1310 nm device. FIG. 8 shows the variation of refractive index vs. depth along the axis of laser oscillation for an example 1310 nm design with four standing wave maxima between the two mirrors. The periodic structure at the left of FIG. 8 represents the fully oxidized mirror and the periodic structure at the right of FIG. 8 represents the suspended dielectric mirror including the thicker first layer which is the silicon nitride membrane. The MQW gain region and airgap tuning region between the mirrors are also indicated in FIG. 8.

The features described in the preceding paragraph apply not only to VCSELs in the 1310 nm range but similar principles can be applied across the 1150-2500 nm wavelength range, which can use an InP-based gain region in conjunction with a GaAs-based mirror region. The 1200-1400 nm range is particularly important for many swept source optical coherence tomography applications, such as endoscopic applications, vascular imaging, and cancer imaging. The 1800-2500 nm range is important for gas spectroscopy. This latter range preferably uses compressively strained InGaAs quantum wells on Indium Phosphide substrates.

Figure 23:
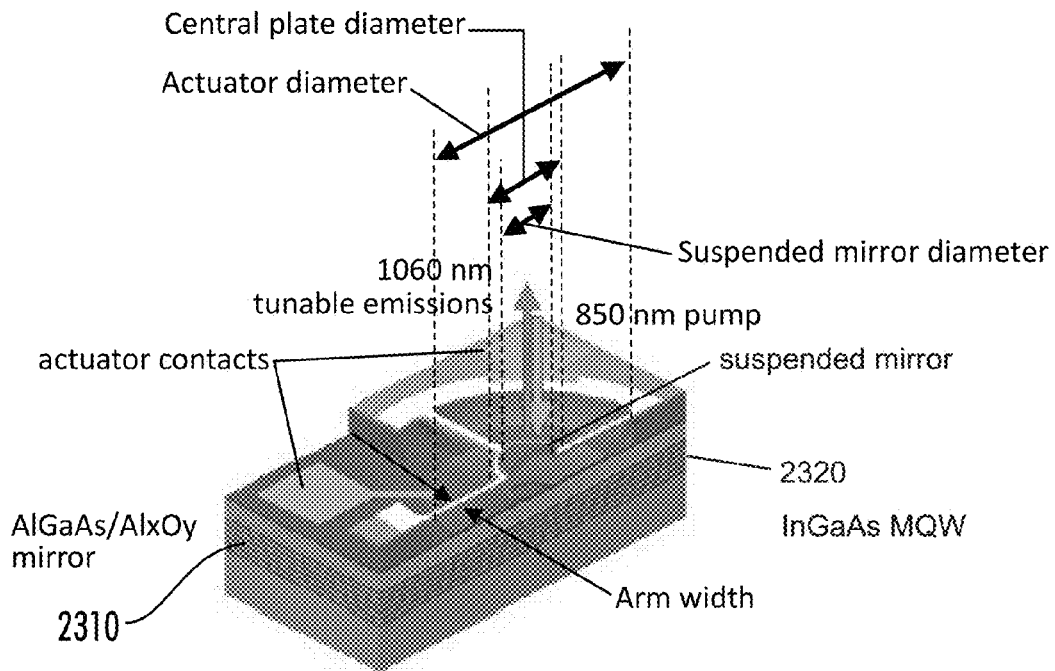
FIG. 23 illustrates a MEMS-VCSEL implementation of a widely tunable short-cavity laser operating near 1060 nm.

FIG. 23 illustrates another MEMS-tunable VCSEL like that of FIG. 7 but instead configured to operate in a wavelength range around 1060 nm. Like the 1310 nm VCSEL, this device employs a fully oxidized AlGaAs/Al$_x$O$_y$ mirror 2310 as the bottom mirror. The aluminum content in the AlGaAs layers of this bottom mirror is preferably >10%, to prevent absorption of the pump beam in the optically pumped structure, which ideally has a pump wavelength around 850 nm. In this case, no wafer bonding is required, since the compressively strained InGaAs quantum wells in the gain region can be epitaxially grown on the same GaAs substrate as the fully oxidized mirror. A non-wafer-bonded structure like FIG. 23 can be configured with other quantum well compositions to access a range of wavelengths in a range from about 600 nm to about 1150 nm. Besides InGaAs, these include but are not limited to AlInGaP, AlInGaAs, InGaAsP, InGaP, AlGaAs, and GaAs. GaAs quantum wells would be used in about the 800-870 nm range, AlGaAs wells in about the 730-800 nm range, AlInGaP and InGaP in about the 600-730 nm range, and InGaAsP or AlInGaAs as alternative materials in about the 800-900 nm range. The wavelength range of 700-1100 nm is of particular interest in SSOCT ophthalmic imaging and also oxygen sensing, and the range of about 990-1110 nm is of greatest interest for ophthalmology.

Figure 24:
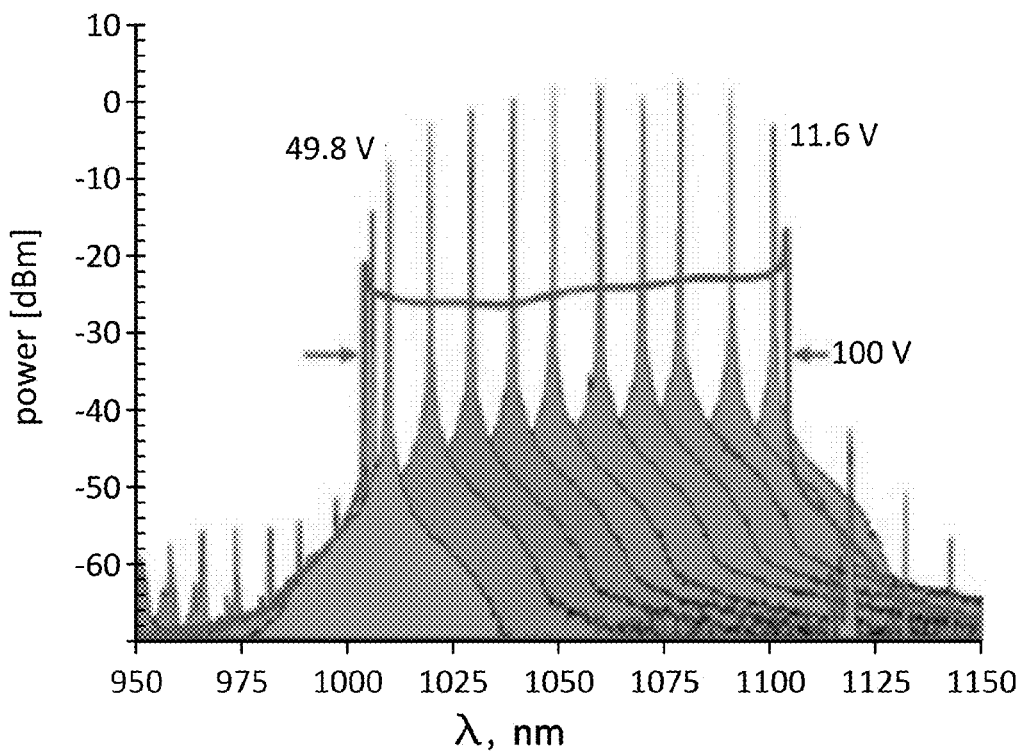
FIG. 24 illustrates static and dynamic tuning spectra of the MEMS-VCSEL in FIG. 23.

As in the case of the 1310 nm structures, periodic gain can be employed in the structure of FIG. 23. In the 990-1110 nm range, it is advantageous to use a periodic gain structure with three InGaAs quantum wells 2320 at three standing wave peaks in the cavity, separated by GaAs barriers which absorb the pump radiation and generate electrons and holes which diffuse into the quantum wells. Typical quantum well widths are 6-12 nm and typical Indium percentage is about 20%. Quantum well widths greater than about 8 nm lead to a second confined quantum state and broadened gain. A structure using this approach generated the tuning results shown in FIG. 24, illustrating a tuning range of 100 nm around 1060 nm. The FSR of this structure is around 100 nm or about 9.4% of the center wavelength. FSR can be increased to >10% as in the 1310 nm structure by placing all quantum wells on a single standing wave peak or by placing four quantum wells on two standing wave peaks. In these latter cases, strain compensation of the InGaAs with tensile-strained GaAsP, as described in the prior art on fixed wavelength VCSELs (Hatakeyama, H., Anan, T., Akagawa, T. et al., "Highly Reliable High-Speed 1.1-mu m-Range VCSELs With InGaAs/GaAsP-MQWs," IEEE Journal of Quantum Electronics, 46(6), 890-897 (2010)) can be employed.

Both the structure of FIG. 7 and that of FIG. 24 achieve a tuning range that is >90% of the FSR of the device, as shown in the associated results of FIGS. 9 and 24 respectively. Also shown in FIGS. 9 and 24 is a suppression of transverse modes, manifesting themselves as a shoulder 1-3 nm away from the main peak, which is generally >40 dB below the main peak. In an optically pumped structure employing a single transverse mode pump beam, the transverse mode suppression can be increased to >45 dB across the tuning range if the pump beam is well-aligned along the optical axis of the half-symmetric cavity of FIG. 1.

The specific implementation of the embodiments in FIGS. 7, 9, 23, 24 employs materials and wavelength ranges associated with GaAs and InP substrates. Other materials could be used to implement some embodiments of the present invention. For example, tunable emission in about the 2000-2500 nm mid-infrared range could be obtained using materials on GaSb substrates, as prior art researchers have done with fixed wavelength VCSELs in (Kashani-Shirazi, K., Bachmann, A., Boehm, G. et al., "MBE growth of active regions for electrically pumped, cw-operating GaSb-based VCSELs," Journal of Crystal Growth, 311(7), 1908-1911 (2009)). Alternately, a tunable short-cavity laser according to an embodiment of the present invention operating in the 400-550 nm range could be realized using materials grown on GaN substrates as described by researchers making fixed wavelength VCSELs (Higuchi, Y., Omae, K., Matsumura, H. et al., "Room-Temperature CW Lasing of a GaN-Based Vertical-Cavity Surface-Emitting Laser by Current Injection," Applied Physics Express, 1(12), (2008)). Implementation of embodiments of the present invention in the visible range of 400-700 nm range has application in optical metrology tools and biological and medical spectroscopy.

Figure 14:
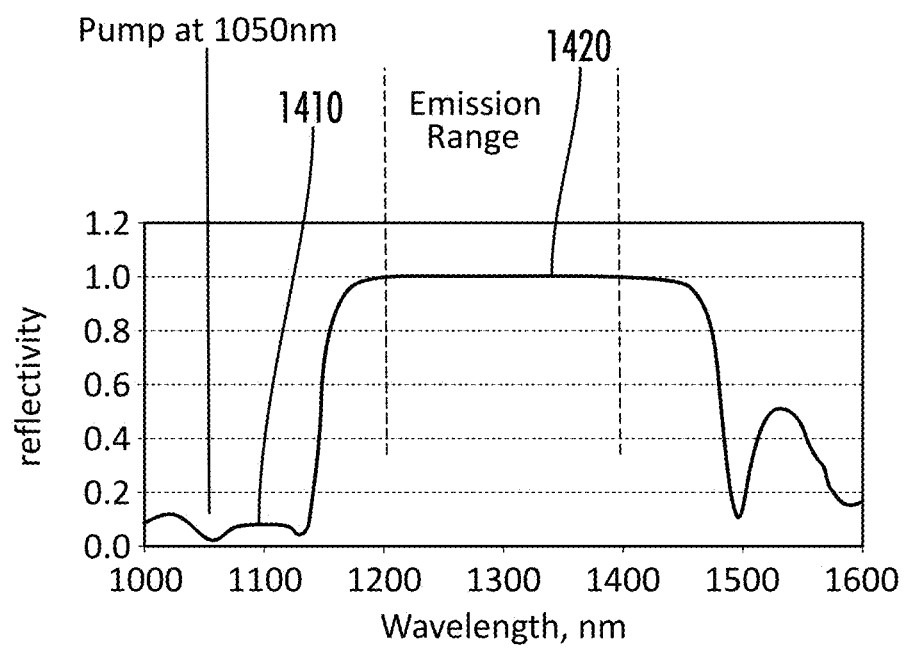
FIG. 14 illustrates a 1310 nm reflectivity spectrum configured to support pumping at 1050 nm.

One preferred embodiment for all the wavelength ranges indicated above is an optically pumped embodiment in which an optical pump supplies energy for lasing, as in many examples already discussed. For operation in the 550-700 nm range, the optical pump wavelength is preferably in a range of about 400 nm to about 600 nm. For operation in the 700-1100 nm range, the preferred pump wavelength is in a range of about 600-1000 nm. For operation in the 1200-1400 nm range, the preferred pump wavelength is in a range of about 700-1200 nm. For operation in the 1800-2500 nm range, the preferred pump wavelength is in a range of about 1000-2000 nm. We note that it is often advantageous to pump through the top mirror, as indicated in the 1050 nm MEMS-VCSEL of FIG. 24. Side pumping around the mirror is also possible, but pumping through the top mirror leads to a more compact package. In this case the top mirror needs to have minimal reflectivity at the pump wavelength. FIG. 14 illustrates an example top mirror designed reflectivity for a tunable short-cavity laser configured to emit in the range of 1200-1400 nm, with an optical pump at 1050 nm. As shown in FIG. 14, the top mirror can be made to have minimal reflectivity 1410 at the pump wavelength at 1050 nm, while having high reflectivity 1420 at the desired 1200-1400 nm emission wavelength range.

Figure 27:
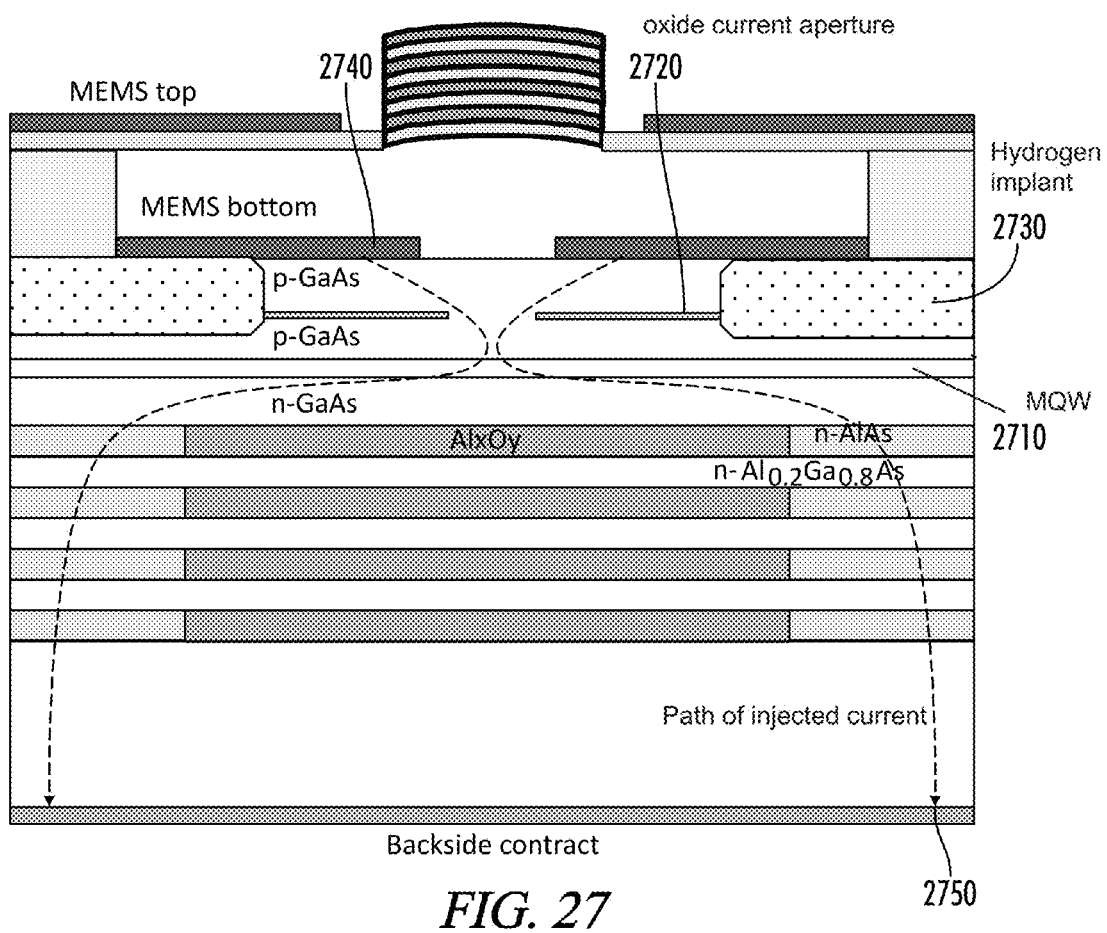
FIG. 27 illustrates an electrically pumped MEMS-VCSEL implementation of a widely tunable short-cavity laser.

Although the above has been primarily described with respect to optically pumped devices, transition from optical pumping to electrical pumping can use well-known processing methods for vertical cavity lasers. An example electrically pumped structure according to an embodiment of the present invention is illustrated by FIG. 27, which is a MEMS-tunable VCSEL with GaAs-based MQW gain region 2710 and a fully oxidized mirror, as in the 1060 nm example of FIG. 24. As shown in FIG. 27, the bottom MEMS contact 2740 also functions as the top laser diode contact. In the optically pumped structure, the confinement of optical carriers is accomplished by the limited lateral extent of the optical pump beam, while in an electrically pumped structure a current aperture 2720 must be provided. This aperture 2720 is usually provided by another partially oxidized layer above the fully oxidized mirror, as shown in FIG. 27. The current aperture could also be provided by a patterned and buried tunnel junction, as has been employed by other researchers. In both cases, care must be taken to engineer the spreading resistance to avoid current crowding, as has been described by prior art researchers in fixed wavelength VCSELs (Scott, J. W., Geels, R. S., Corzine, S. W. et al., "MODELING TEMPERATURE EFFECTS AND SPATIAL HOLE-BURNING TO OPTIMIZE VERTICAL-CAVITY SURFACE-EMITTING LASER PERFORMANCE," IEEE Journal of Quantum Electronics, 29(5), 1295-1308 (1993)).

As shown in FIG. 27, the combination of implant passivation 2730 and oxide current aperturing 2720 enables electrical pumping of the structure. Current conduction proceeds from the middle MEMS contact 2740 through the current aperture 2720, and around the fully oxidized region of the bottom mirror to a backside substrate contact 2750. Carrier recombination in the MQW region, which is preferably comprised of three strain-compensated InGaAs/GaAsP quantum wells, produces gain for lasing.

Figure 22:
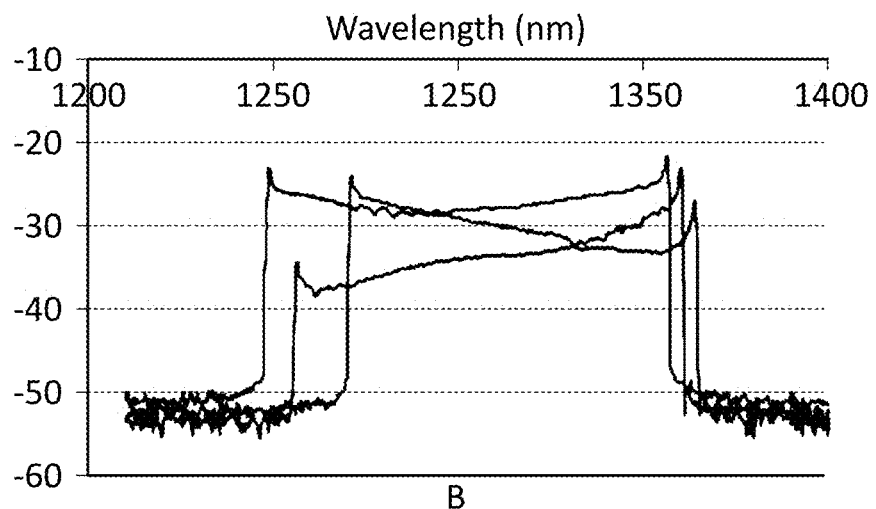
FIG. 22 illustrates various output power spectra of a widely tunable short-cavity laser operating near 1310 nm.

For many applications of interest, it is desirable to control the spectral shape of the output power spectrum emerging from the tunable short cavity laser. This output power shaping can be accomplished in a variety of ways. One method is by controlling the shape of the top mirror reflectivity spectrum. Generally, regions of lower reflectivity allow more light out of the optical cavity, while regions of higher reflectivity allow less light out of the optical cavity. Thus, one can define a target spectral shape or power variation across the wavelength range, and adjust a shape of the mirror reflectivity achieve this spectrum. A target power variation might be a Gaussian shape. FIG. 22 illustrates examples of several spectral shapes that have been achieved in the MEMS-VCSEL implementation of FIG. 7, by adjusting the reflectivity spectrum of the suspended top mirror. These spectra range from power peaked at both edges, power peaked at the blue edge, and power peaked at the red edge. Additional spectral shapes can be achieved by the same method.

Another way of changing the spectral shape is to control the pump energy into the gain region dynamically during wavelength tuning. In the case of an optically pumped device, this can be controlling the pump energy into the device, and in the case of an electrically pumped device the drive current would be controlled. Shaping of the pump energy can also improve thermal management of the device.

Figure 12:
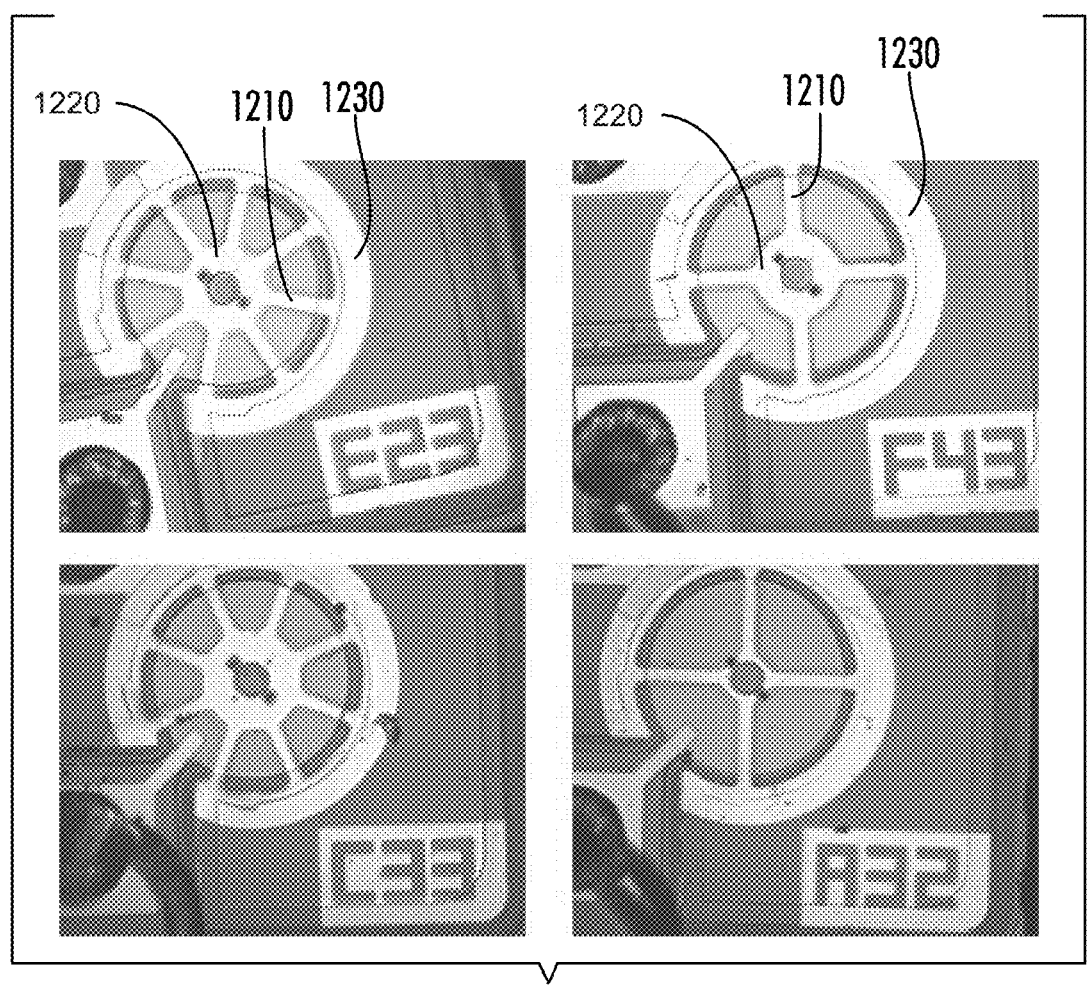
FIG. 12 illustrates various actuator geometries.

For the particular embodiment that uses a MEMS actuator, further details of the MEMS actuator design can be implemented to enhance the device performance. As mentioned above, the deformable dielectric membrane is preferably made of silicon nitride, and a tensile stress of 100-1000 MPa is preferred to give a substantially increased resonant frequency relative to a no-stress design, and to minimize bowing of the membrane upon release. By resonant frequency, we are referring to the lowest order mechanical mode of the device, which corresponds to the desired "piston" motion of the actuator. This is an important parameter of the device performance. One preferred actuator geometry is a central plate with supporting arms, as shown in FIG. 7, FIG. 12, and FIG. 23. Important parameters of this particular geometry are the actuator diameter, central plate diameter, arm width, and suspended mirror diameter, as shown in FIG. 23. Using an actuator diameter of about 220 µm, between four and eight supporting arms, an actuator arm width of about 16 µm, a suspended mirror diameter of about 34 µm, a suspended mirror comprised of about 11 periods of $SiO_2/Ta_2O_5$ centered at 1310 nm, a central plate diameter varying from about 50 µm to about 110 µm, and a ¾ wavelength silicon nitride membrane with stress in a range of about 200 MPa to about 450 MPa, it is possible to obtain a variety of frequency responses represented by the sampling of FIG. 10. FIG. 12 shows pictures of a sampling of actuator geometries resulting in the frequency responses of FIG. 10. In FIG. 12, top-view pictures of several MEMS tunable VCSEL structures having four or eight supporting struts 1210. FIG. 10 shows the tuning of a MEMS-VCSEL wavelength as a function of drive frequency applied to the MEMS-actuated airgap tuning mechanism. As shown, the resonant frequencies are in a range of about 200 kHz to about 500 kHz, and the 6 dB bandwidths of the fastest devices are approaching 1 MHz.

Also shown is a variation in the damping of the actuator, manifested by varying amounts of peaking at resonance. The damping is primarily caused by squeeze-film damping, which represents interaction with viscous air. As the actuator area is increased or the airgap is reduced, the squeeze-film damping goes up, flattening the frequency response. A flat wide frequency response is desirable for variable speed drive, and for linearization of drive through multiple harmonics. Though damping through squeezed film effects is demonstrated in FIG. 10 in a MEMS device, similar effects can be seen in other airgap tuned devices such as piezo-driven devices. In general, it is possible to control the damping of the MEMS actuator through a variety of methods, including changing the actuator area or shape to change interaction with viscous air, changing the background gas composition or gas pressure, which further changes the contribution of squeeze-film damping, changing the airgap thickness, and changing the size of holes or perforations in the actuator to change the regime of fluid flow through the holes from a turbulent to a non-turbulent regime. Additionally, annealing the actuator can change the stress of various materials in the actuator, which will have an effect on damping.

The frequency responses represented by FIG. 10 are representative and not limiting. The resonance frequency can be increased by stiffening the membrane through increased tensile stress, increased thickness (for example 5/4 wavelength), reduced suspended mirror diameter and thickness, or shortened arms, such that 6-dB bandwidths in excess of 2 MHz can be achieved, as can be calculated by those skilled in the art of finite element modeling. Similarly, resonant frequency can be decreased well below 100 kHz by changing the same parameters in the opposite direction. We also note that other geometries are possible, such as a spiral arm geometry, which reduces resonant frequency, or a perforated membrane without clearly delineated supporting struts. Referring to FIG. 12, if the diameter of the central plate 1220 is expanded to the outer ring 1230 actuator diameter, and perforations are added, we achieve a perforated membrane without clearly delineated supporting struts.

The silicon nitride membrane discussed above is highly insulating, and may therefore be prone to charging and electrostatic drift. Introducing a small amount of electrical conductivity in the membrane can reduce the propensity to charging. For silicon nitride, this electrical conductivity can be introduced by using a non-stoichiometric silicon-rich film, or by doping the silicon nitride film with silicon.

The tuning results presented in FIGS. 9 and 24 indicate the voltages required to tune the device, noted alongside the spectra. These voltages range up to about 65 V for full tuning over on FSR, corresponding to a membrane deflection of about half the center wavelength or about 650 nm for 1310 nm devices and 525 nm for 1050 nm devices. These voltages are associated with the MEMS actuator dimensions and silicon nitride stress levels indicated above, and with reference to FIGS. 10 and 12, along with a nominal zero-voltage airgap in the range of about 1.6 µm.

We also note that faster tuning mechanisms than mechanical contraction or expansion of an airgap can be employed such as carrier injection tuning in semiconductors, which can be in the GHz range. This mechanism, however, is typically limited to about a 1% change in optical path length, so is not suitable for large tuning ranges.

A number of additional structural and performance features of an embodiment of the present invention can be understood with further reference to FIGS. 1 and 2. For many applications, it is desirable to have the intensity vs. wavelength profile, shown in FIG. 2, to be free of periodic variation. The present disclosure describes a short-cavity tunable laser with a ripple that is less than about 1% of an average power. The term "ripple" is commonly used to describe these variations. Depending on the spectral period of this ripple, and depending on the application, it may have varying degrees of adverse effect. For example, in a swept source OCT (SSOCT) system, ripple of a particular spectral period having an amplitude of 1% or more relative to an average power can manifest itself as a spurious reflector at an apparent distance in an SSOCT image. Ripple is typically caused by spurious reflections outside the laser cavity. These reflections can come from coupling lenses or other optical elements in the optical system, or they can come from substrate reflections in a vertical cavity laser. For example, in the laser of FIG. 7, reflections coming from below the second mirror, such as from the bottom of the GaAs substrate 770 on which this device is disposed, can cause ripple. The substrate reflection amplitude can be suppressed by various means, including but not limited to increasing the reflectivity of the second mirror, introducing loss through dopants in the substrate, increasing substrate thickness, or roughening the backside of the substrate to increase scattering. An optimal grit for substrate roughening to increase scattering is a grit size >30 µm in the range of 900-1400 nm tunable emission. In addition, use of a fully oxidized bottom mirror having 7 or more periods, which has a theoretical lossless reflectivity of >99.5%, can suppress ripple to <1% levels.

Another important performance feature of an embodiment of the present invention is operation in a fixed polarization state throughout a tuning range of the wavelength swept emission. Semiconductor lasers in which lasing emission occurs perpendicular to the plane of a strained quantum well, such as vertical cavity lasers, have no natural preferred polarization unless some non-symmetry is introduced into the cavity. Operation in a single polarization state is important if operating with any polarization-sensitive components in the optical system, such as polarization-selective optical amplifiers. Such systems may also employ the polarization stable device according to an embodiment of the present invention in combination with polarization maintaining fiber. Polarization switching over the emission wavelength range can cause power dropouts or image artifacts in an SS-OCT system, and compromise dynamic coherence length. Having a well-defined polarization state would also allow a laser system to be constructed that requires alternating polarization states.

Operation in a single polarization state throughout a tuning range of the device can be accomplished in a variety of ways. One way is to introduce one or more nanowires integral with the optical cavity of the device. With respect to FIG. 7, this nanowire can be disposed on top of the MQW gain region 780 adjacent the tunable airgap, in the center of the optical path. Alternatively it could be placed on top of the suspended mirror. A nanowire is an element which can cause polarization-dependent scattering or absorption of light. Typical dimensions might be 50 nm wide, several microns long, and 10 nm thick. The nanowire might be constructed of metal or may simply be a refractive index perturbation. Typically light polarized along the long direction of the nanowire interacts with a different strength than that polarized perpendicular to the nanowire. Since laser cavities require small amounts of loss anisotropy for mode selection, a single intra-cavity nanowire is sufficient to suppress one polarization while maintaining low loss in another polarization. The loss in different polarizations for a nanowire can be calculated by known means to those skilled in the art as described for example in (Wang, J. J., Zhang, W., Deng, X. G. et al., "High-performance nanowire-grid polarizers," Optics Letters, 30(2), 195-197 (2005)). Having a grid of nanowires creates greater loss anisotropy, but also increases loss for the preferred polarization. So in for example a VCSEL cavity, excess loss introduced in the preferred polarization should be <0.1%. This suggests one or a very small number of nanowires. In the case of a VCSEL or VCL, ideally the nanowire should be aligned with the crystal axes of the semiconductor on which the VCSEL is disposed. This typically means the [110] direction or perpendicular to the [110] direction for wafers grown on (100) or near (100) orientation. The reason for this is that a weak polarization selection effect exists to align the VCL polarization along one of the crystal axes, and any further polarization control method should strive to add to rather than compete with this effect.

Figure 13:
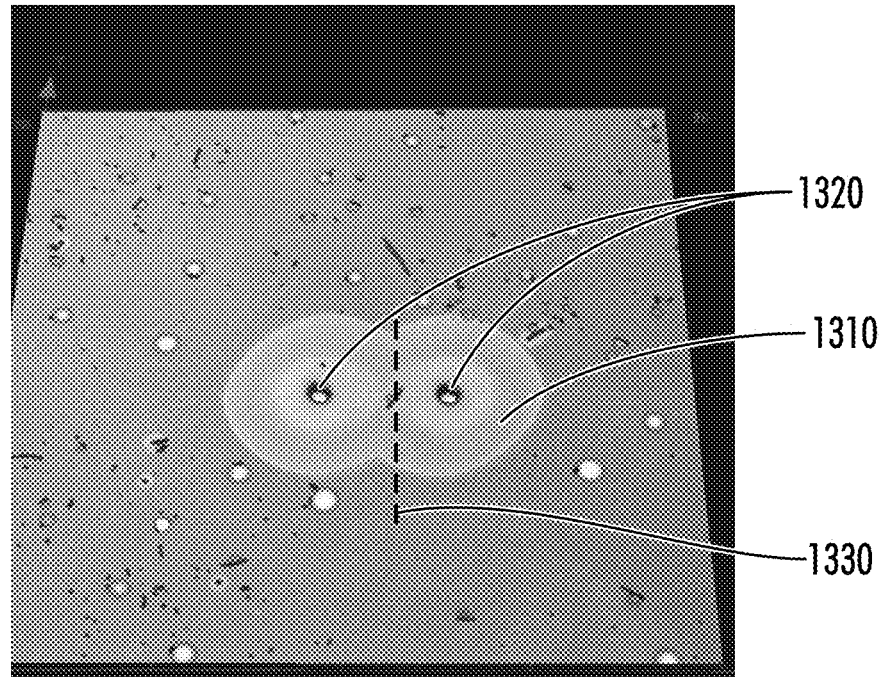
FIG. 13 illustrates oxidation for a fully oxidized mirror proceeding from two etched holes.

Other means of polarization control include introduction of anisotropic stress, as in (Matsui, Y., Vakhshoori, D., Peidong, W. et al., "Complete polarization mode control of long-wavelength tunable vertical-cavity surface-emitting lasers over 65-nm tuning, up to 14-mW output power," IEEE Journal of Quantum Electronics, 39(9), 1037-10481048 (2003)), lateral current injection as described in fixed wavelength VCSELs (Zheng, Y., Lin, C. H., and Coldren, L. A., "Control of Polarization Phase Offset in Low Threshold Polarization Switching VCSELs," IEEE Photonics Technology Letters, 23(5), 305-307 (2011)), or use of a noncircularly symmetric oxidation process to create the fully oxidized mirror of FIG. 7, as described with respect to FIG. 13. As shown in FIG. 13, oxidation 1310 proceeds outward from two etched holes 1320, and oxidation fronts meet along a line shown by the dashed line 1330 in the figure. Along this dashed line is a 5 nm dip, which forms a refractive index nanowire, which can select the VCSEL polarization. The refractive index nanowire of FIG. 13 will be aligned with the crystal axes as long as the holes are aligned with the crystal axes.

Further enhancement of polarization control can be obtained in wafer-bonded devices by ensuring that crystal axes of the bonded wafers are aligned during the bonding process. Since one crystal axis may be slightly preferred over another, aligning crystal axes during bonding leads to multiplication of this effect, rather than cancellation of the effects by crossing the alignments.

Figure 28:
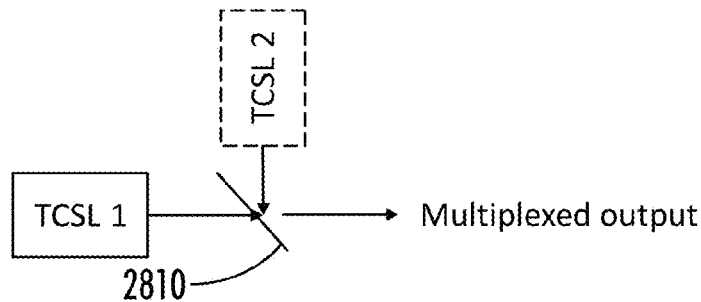
FIG. 28 illustrates wavelength sweeps from two short-cavity lasers interleaved to produce a multiplied sweep rate.
Figure 28:
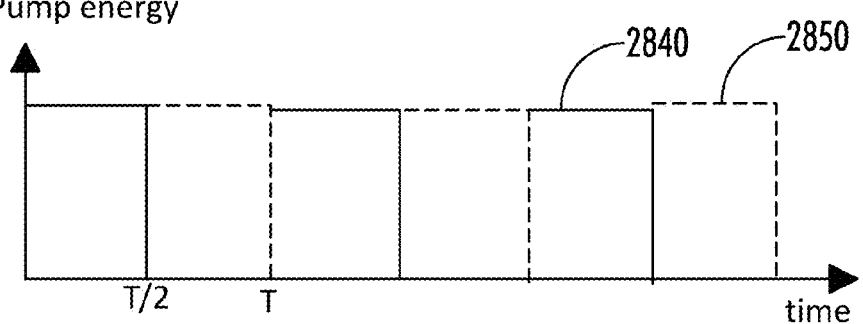
Figure 28:
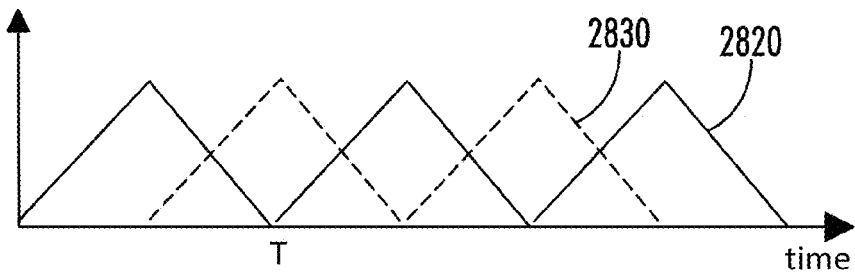
Figure 28:
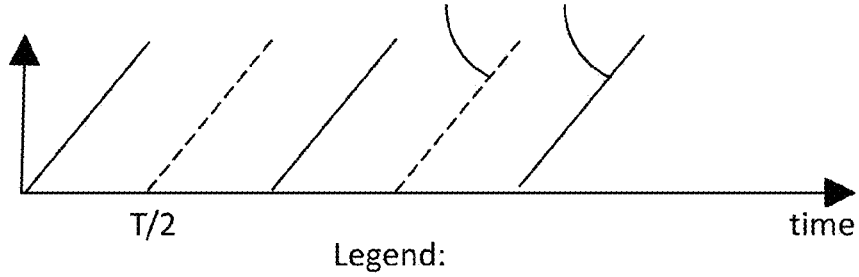

The tunable short-cavity laser described here can be combined in array form to generate an aggregate tunable laser source with enhanced optical properties. In the particular implementation where the laser is a MEMS-tunable vertical cavity laser, the array can be fabricated in monolithic form. One example of such combination of particular utility in SS-OCT is described with the aid of FIG. 28. As shown in FIG. 28A, a first tunable short cavity laser TCSL 1 and a second tunable short-cavity laser TCSL 2 are multiplexed on to a common optical path, using a beam splitter, fiber coupler or other know combining element 2810. Each TCSL is driven to have a bidirectional tuning over its tuning range, as shown by the solid wavelength trajectory 2820 in FIG. 28C for TCSL 1 and the dashed trajectory 2830 in FIG. 28C for TCSL 2. Each laser is repetitively scanned at a repetition period T, but the scan of TCSL 2 is time-delayed relative to that of TCSL 1 by half the repetition period. In addition, the pump energy 2840, 2850 (either electrical or optical pump) for each of the two TCSLs is turned off during the backward wavelength scan such that only the forward or front of half of the wavelength scan, when pump energy is non-zero, emits laser radiation. In some instances, if the FSR is much larger than the gain bandwidth of the supporting material, scanning the tuning element beyond the material gain bandwidth will automatically shut off the laser without having to turn off the pump energy.

The wavelength trajectory of the multiplexed output is shown in FIG. 28D, comprising components from both TCSL 1 (solid) 2860 and TCSL 2 (dashed) 2870, and illustrating unidirectional scanning at a new repetition period T/2 which is half the original period T of each TCSL. In this way, the sweep rate has been multiplied by a factor of two. The same principle could be applied to N lasers and multiplication of the sweep rate by a factor of N. The principle of interleaving TCSLs can also be used for more than multiplying sweep rate, but also for multiplying tuning range, interleaving different tuning ranges, tuning speeds, or tuning trajectories, or a for a variety of other purposes evident to those skilled in the art of SSOCT, spectroscopy, communications, or optical detection.

The tunable short-cavity laser described thus far can be combined with an optical amplifier to create an amplified tunable source with increased output power and other advantageous properties for imaging. The amplifier can be a semiconductor amplifier, a fiber amplifier such as a praseodymium-doped fiber amplifier for operation in a window around 1300 nm, an Ytterbium-doped amplifier for operation in a window around 1050 nm , a Fluoride-doped extended bandwidth fiber amplifier near 1050 nm, or any kind of optical amplifier. The use of an amplifier can also enable the interleaving scheme above, wherein a high extinction ratio optical amplifier can be used to turn on one source at the appropriate time, instead of turning off the pump energy to that source.

Figure 15:
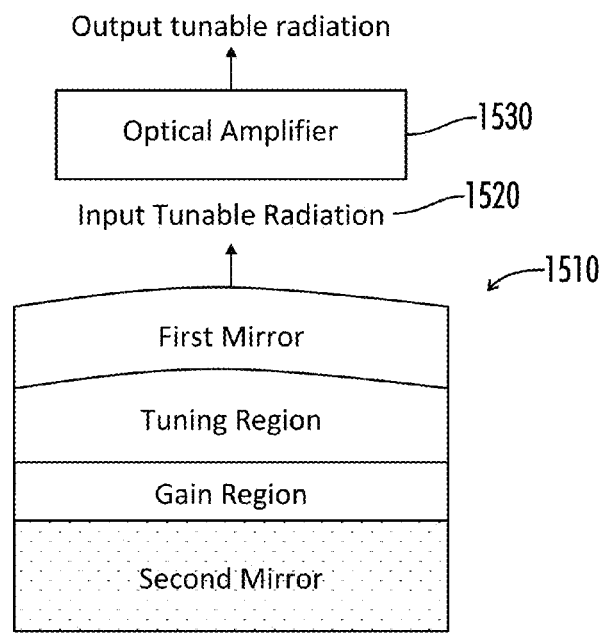
FIG. 15 illustrates an embodiment of a widely tunable short cavity laser coupled to an optical amplifier.

One basic configuration is illustrated in FIG. 15, in which a tunable short cavity laser 1510 according an embodiment of the present invention emits an input tunable radiation 1520 directed to an input side of the optical amplifier 1530. This input tunable radiation has an input average power, input power spectrum, input wavelength range, and input center wavelength. The amplifier amplifies the input tunable radiation to generation an output tunable radiation having an output average power, output center wavelength, output wavelength range, and output power spectrum.

Figure 21:
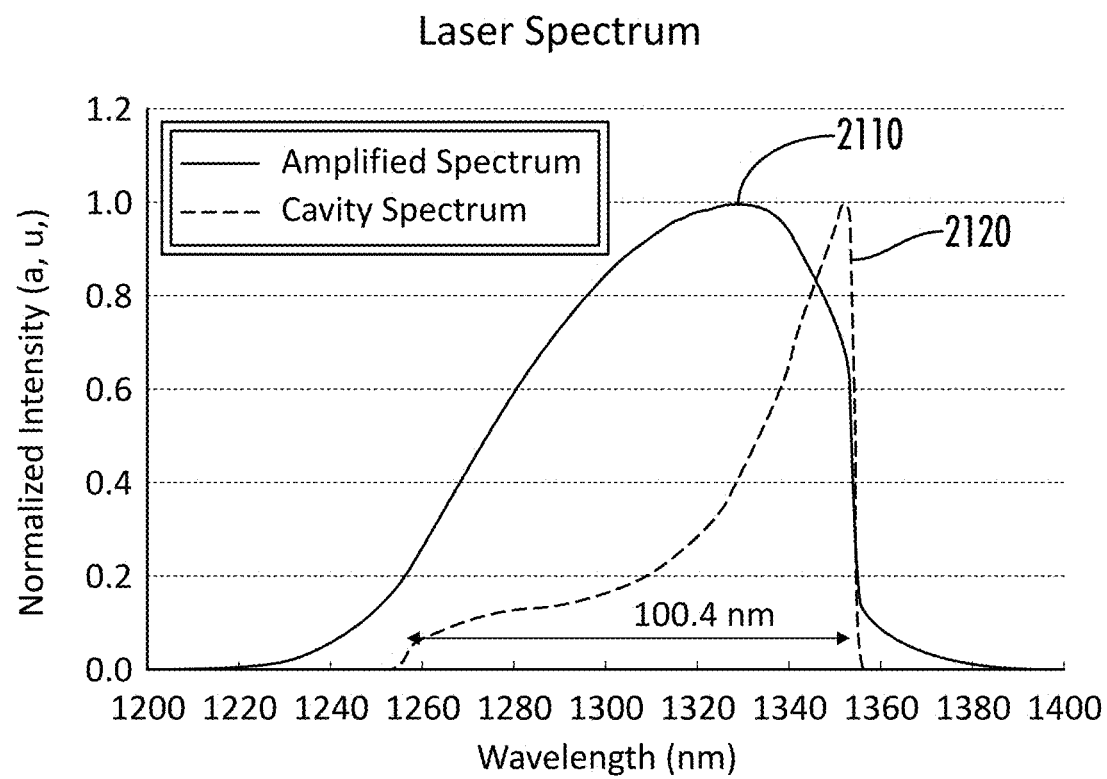
FIG. 21 illustrates an amplified and pre-amplified spectrum of a widely tunable short cavity laser.

In the preferred embodiment, the amplifier is operated in a saturated regime, as is well-known to those skilled in the art of optical amplifiers. The saturated regime can suppress noise fluctuations present in the input tunable radiation, and can also provide advantageous spectral shaping in which a full-width at half-maximum (FWHM) of the output tunable radiation can exceed a FWHM of the output tunable radiation. An example of this is shown in FIG. 21, in which the amplified tunable spectrum 2110 has a wider FWHM than the input tunable radiation 2120 from the tunable short cavity laser.

Figure 16:
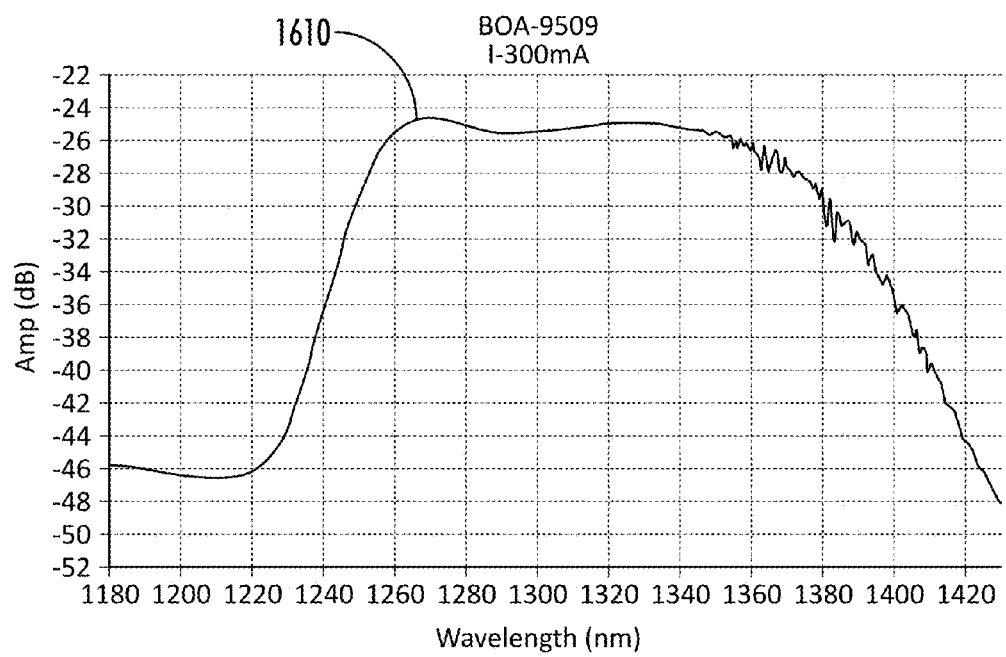
FIG. 16 illustrates an ASE spectrum from a dual-quantum state semiconductor optical amplifier.

In the preferred embodiment the optical amplifier is a semiconductor quantum well amplifier, which can provide low noise, wide gain-bandwidth, and high gain. Semiconductor quantum well amplifiers can also provide very high extinction ratio >40 dB, which can be used as a switch to gate devices on and off as described above. The quantum well is preferably configured to have two confined quantum states to support a wider gain bandwidth. FIG. 16 illustrates amplified spontaneous emission from a dual quantum state semiconductor optical amplifier at 1310 nm, comprising three AlInGaAs compressively strained quantum wells, illustrating a hump 1610 at the shorter end of the spectrum corresponding to second quantum state widening of the spectrum. The 3-dB spectral width of this amplified spontaneous emission (ASE) is 110 nm, suggesting a 3 dB small signal gain bandwidth of similar value.

The semiconductor optical amplifier can be configured to be polarization sensitive, by using all compressively strained or tensile-strained quantum wells, or polarization insensitive by using both types of strain in a single structure to provide gain at all polarizations.

In the preferred configuration, the center wavelength of the input tunable radiation is at a longer wavelength than a center wavelength of amplified spontaneous emission (ASE) emitted by the amplifier. The amplifier ASE is typically blue-shifted relative to the amplifier gain spectrum, so this configuration brings the spectrum of input tunable radiation into more optimal alignment with the amplifier gain spectrum. In general, varying the alignment of the amplifier ASE relative to the input power spectrum can provide advantageous spectral shaping.

The basic configuration of FIG. 15 can be augmented with various forms of filtering to create a lower noise amplified swept source. Many swept source laser application in metrology, spectroscopy, and biophotonics would benefit from the suppression of broadband ASE, and an improvement in side mode suppression. The addition of an additional tunable spectral filter to the system, either internal to the laser cavity, between the laser and amplifier, or at the output of the system is one means of providing improved performance in this regard. In one preferred embodiment, the amplifier shown in FIG. 15 can be a tunable resonant amplifier, such as a vertical cavity amplifier described by (Cole, G. D., Bjorlin, E. S., Chen, Q. et al., "MEMS-tunable vertical-cavity SOAs," IEEE Journal of Quantum Electronics, 41(3), 390-407 (2005)), which only amplifies at a narrow band of wavelengths, and is synchronously tuned with the input tunable radiation of the tunable short cavity laser, such that the passband of the amplifier is always matched to the input tunable radiation wavelength.

Figure 17:
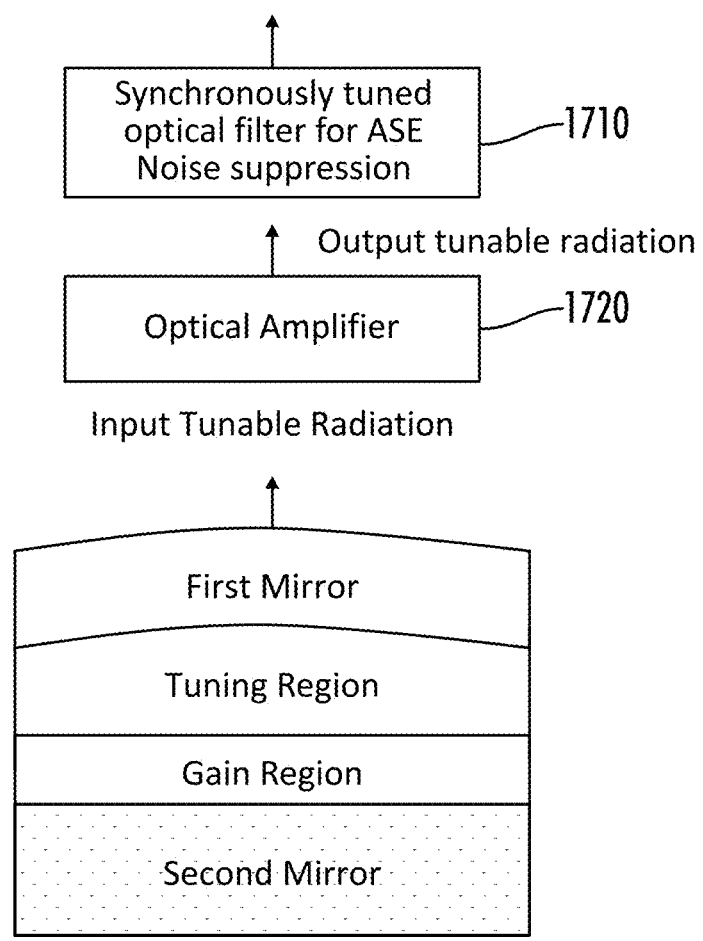
FIG. 17 illustrates a widely tunable short cavity laser coupled to an optical amplifier, the output of which is coupled to a synchronously tuned optical filter.
Figure 18:
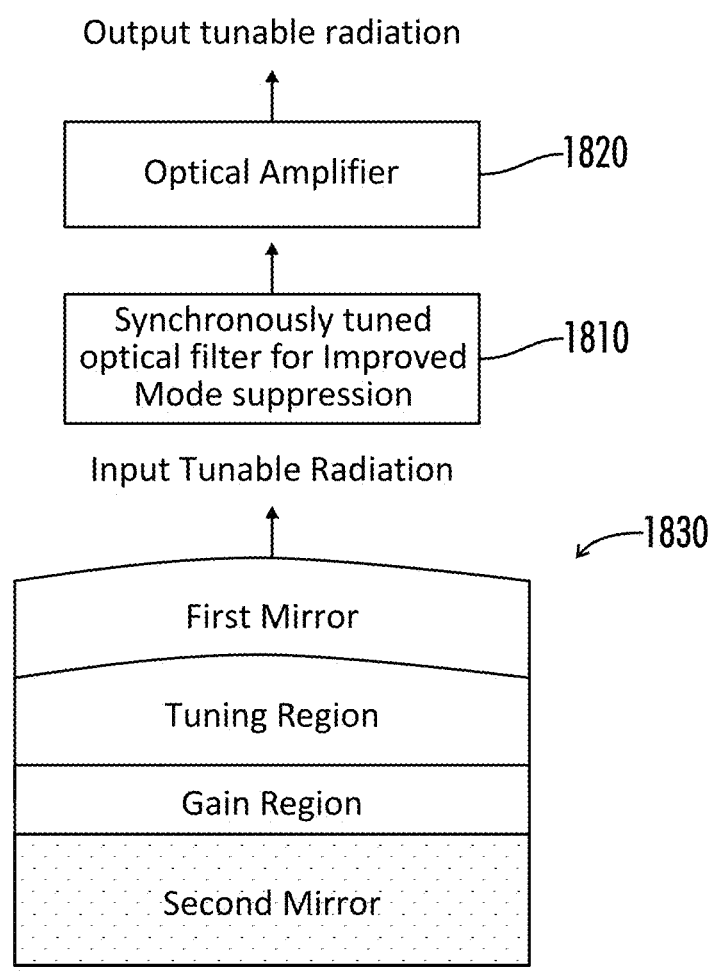
FIG. 18 illustrates an amplified widely tunable short cavity laser with a tunable optical filter between the laser and amplifier.

A number of other preferred configurations are illustrated by FIGS. 17-20. In FIG. 17, a synchronously tuned optical filter 1710, whose passband is aligned at all times with the wavelength of the input tunable radiation, is placed after the broadband optical amplifier 1720 to reduce residual ASE noise and improve a signal to noise ratio of the amplified tunable radiation. In FIG. 18, the same synchronously tuned optical filter 1810 is placed between the tunable short cavity laser 1830 and the optical amplifier 1820, to improved a side-mode suppression of the input tunable radiation prior to amplification.

Figure 19:
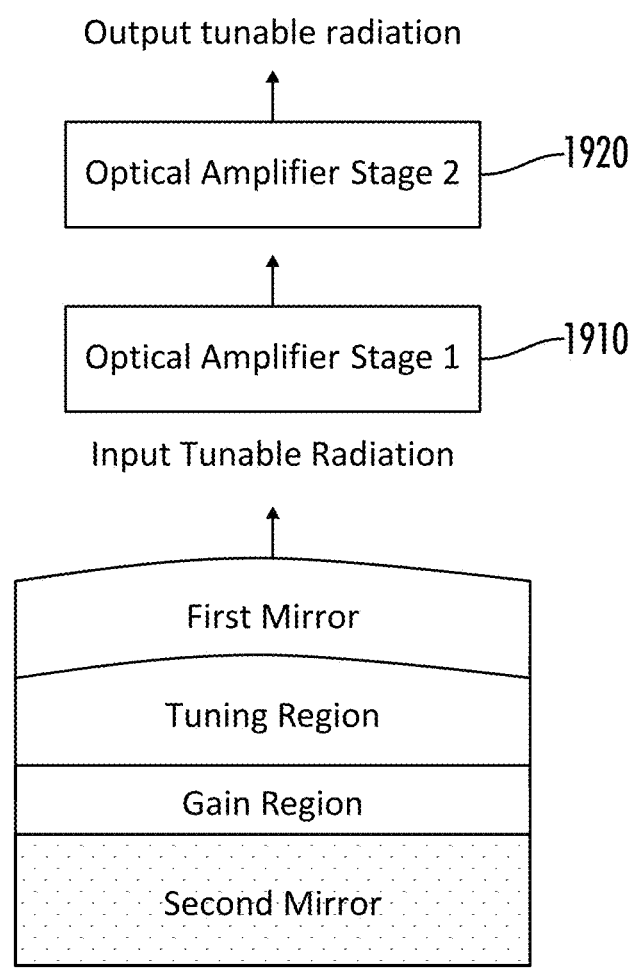
FIG. 19 illustrates an embodiment of a widely tunable short cavity laser with two amplification stages.

Another configuration is illustrated in FIG. 19, where two amplification stages 1910, 1920 are used. These can be implement as two separate amplifiers, or as a single waveguide amplifier with split amplifier contacts. The use of two amplification stages 1910, 1920 provides further flexibility in spectral shaping. For example, the gain spectrum of the two amplifiers can be shifted relative to each other, either by biasing identical epitaxial structures differently, or by using different epitaxial structures in the two amplifiers. The use of two amplification stages can also create higher gain and greater output power.

Figure 20:
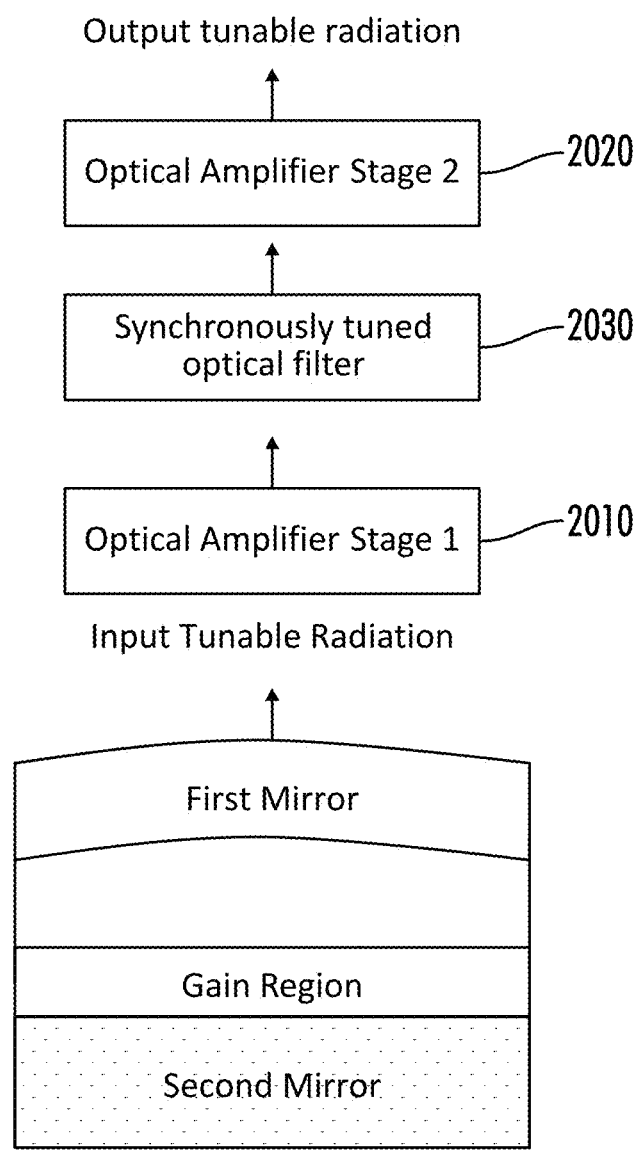
FIG. 20 illustrates an embodiment of a widely tunable short cavity laser with two amplification stages and a tunable optical filter between the stages.

FIG. 20 illustrates yet another two-stage amplifier configuration in which a synchronously tuned optical amplifier 2030 is placed between the two amplifier stages 2010, 2020. This will serve to provide an improved signal to noise ratio of the output tunable radiation.

In most cases of practical interest, in optical systems such as SSOCT and optical spectroscopy, the preferred range of input average powers is about 0.05-2 mW, resulting in a preferred range of output average powers of about 10-120 mW. The exact numbers depend on the gain and saturation power of the amplifier, but this range generally produces amplified tunable radiation with good signal to noise ratio for optical systems.

The basic configuration of the tunable short-cavity laser in combination with an amplifier can be realized with semiconductor optical amplifiers employing a variety of materials appropriate for a variety of wavelength ranges. For example, the amplifier can operate in the 1200-1400 nm range appropriate for SSOCT and water vapor spectroscopy. In this range, use of an AlInGaAs or InGaAsP quantum well on InP produces the required gain. Alternately, the amplifier can operate in about the 800-1100 nm range appropriate for ophthalmic SSOCT, employing at least one compressively strained InGaAs quantum well.

The tunable short cavity laser described in this disclosure has utility in a large number of optical systems, some of which have been briefly alluded to in the preceding description. A few representative examples of those systems are herein now described. A system for SSOCT can employ a tunable laser comprising the tunable short-cavity laser described above, in combination with a means for splitting tunable radiation from the tunable laser to a reference path and a sample path, and an optical detector configured to detect an interference signal between light reflected from said sample and traversing said reference path. Signal processing of this interference signal can then be used to reconstruct structural or compositional information about he sample, as is well-know to those skilled in the art of SSOCT.

A system for optical spectroscopy can employ the tunable short-cavity laser described, in conjunction with an optical detector, to measure an absorption, transmission, scattering, or reflection spectrum of a sample, which can be a solid, liquid, gas, plasma, or any substance in any state of matter. In addition, the variable tuning speed of the tunable short cavity laser can be used to scan across an optical spectrum at variable speed, slowing down information rich regions and speeding up in less-information rich regions, to obtain a desired signal to noise ratio while minimizing measurement time.

The tunable short cavity laser described can, in combination with a dispersive optical element, be employed in a system for optical beam steering. For example, it is well-known that the diffraction angle of a grating is a function of the wavelength of input tunable radiation. Thus, tuning the radiation will scan the diffraction angle and achieve optical beam steering. Other dispersive elements such as prisms can also be employed.

Other optical systems which can employ a short-cavity laser according to an embodiment of the present invention include a distance interferometer, where switching between two or more wavelengths can be used to infer distance.

An embodiment of the present invention can also be used to create a tunable oscillator, by beating the tunable output of the short-cavity laser with a fixed wavelength reference laser. This beating can be accomplished by, for example, an optical detector that responds to incident optical power. If two collinear laser beams impinge on this detector, the detector output will oscillate at the difference in optical frequencies between the two laser beams, provided that difference frequency is within the detector bandwidth. As one laser is tuned, this difference frequency will also tune, creating a tunable oscillator down-shifted from optical frequencies to lower frequencies.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A high speed swept source comprising:
a first tunable laser; and
a second tunable laser;
wherein each of said first and second tunable lasers is configured to emit tunable radiation over an emission wavelength range having a center wavelength, with an output power spectrum over said emission wavelength range and an average emission power;
wherein each of said first and second tunable lasers comprises:
an optical cavity including a first and second mirror;
a gain region interposed between said first and second mirrors;
a tuning region; and means for adjusting an optical path length of said tuning region;
wherein:
a free spectral range (FSR) of said optical cavity exceeds 5% of said center wavelength;
said tunable laser operates substantially in a single longitudinal and transverse mode over said emission wavelength range; and
said means has a wavelength tuning frequency response with a 6-dB bandwidth greater than about 1 kHz; and
wherein a first wavelength sweep of said first tunable laser and a second wavelength sweep of said second tunable laser are interleaved to produce an interleaved sweep.

2. The high speed swept source of claim 1, wherein a high-extinction ratio optical amplifier is used to gate on and off each of said first and second tunable lasers.

3. The high-speed swept source of claim 1, wherein a pump energy of each of said tunable lasers is used to gate on an off each of said first and second tunable lasers.

4. The high-speed swept source of claim 1, wherein at least one of the first tunable laser or the second tunable laser or both have said FSR larger than the emission wavelength range.

5. The high-speed swept source of claim 1, wherein said means for adjusting an optical path length is configured to adjust a physical length of an airgap; and
a frequency response of said means for adjusting an optical path length has damping substantially increased by squeeze-film damping effects.

6. The high-speed swept source of claim 1, wherein said means for adjusting an optical path length further comprises a suspended mirror having a first diameter disposed on a central plate having a second diameter, wherein said first diameter is less than about half of said second diameter.

7. The high-speed swept source of claim 1, wherein the interleaved sweep has an increased sweep rate compared to the first wavelength sweep or the second wavelength sweep or both.

8. The high-speed swept source of claim 1, wherein the interleaved sweep has an increased emission wavelength range compared to the first wavelength sweep or the second wavelength sweep or both.

9. The high-speed swept source of claim 1, wherein the first wavelength sweep and the second wavelength sweep have different tuning ranges.

10. The high-speed swept source of claim 1, wherein the first wavelength sweep and the second wavelength sweep have different tuning speeds.

11. The high-speed swept source of claim 1, wherein the first wavelength sweep and the second wavelength sweep have different tuning trajectories.

12. A method for generating an interleaved sweep comprising:
generating a first wavelength sweep with a first tunable laser; and
generating a second wavelength sweep with a second tunable laser;
wherein each of said first and second tunable lasers is configured to emit tunable radiation over an emission wavelength range having a center wavelength, with an output power spectrum over said emission wavelength range and an average emission power;
wherein each of said first and second tunable lasers comprises:
an optical cavity including a first and second mirror;
a gain region interposed between said first and second mirrors;
a tuning region; and means for adjusting an optical path length of said tuning region;
wherein:
a free spectral range (FSR) of said optical cavity exceeds 5% of said center wavelength;
said tunable laser operates substantially in a single longitudinal and transverse mode over said emission wavelength range; and
said means has a wavelength tuning frequency response with a 6-dB bandwidth greater than about 1 kHz; and
interleaving the first wavelength sweep and the second wavelength sweep to generate an interleaved sweep.

13. The method of claim 12, further comprising gating on and off each of said first and second tunable lasers with a high-extinction ratio optical amplifier.

14. The method of claim 12, further comprising gating on and off each of said first and second tunable lasers with changes to a pump energy.

15. The method of claim 12, wherein at least one of the first tunable laser or the second tunable laser or both have said FSR larger than the emission wavelength range.

16. The method of claim 12, wherein said means for adjusting an optical path length is configured to adjust a physical length of an airgap; and a frequency response of said means for adjusting an optical path length has damping substantially increased by squeeze-film damping effects.

17. The method of claim 12, wherein said means for adjusting an optical path length further comprises a suspended mirror having a first diameter disposed on a central plate having a second diameter, wherein said first diameter is less than about half of said second diameter.

18. The method of claim 12, wherein the interleaved sweep has an increased sweep rate compared to the first wavelength sweep or the second wavelength sweep or both.

19. The method of claim 12, wherein the interleaved sweep has an increased emission wavelength range compared to the first wavelength sweep or the second wavelength sweep or both.

20. The method of claim 12, wherein the first wavelength sweep and the second wavelength sweep have different tuning ranges.

21. The method of claim 12, wherein the first wavelength sweep and the second wavelength sweep have different tuning speeds.

22. The method of claim 12, wherein the first wavelength sweep and the second wavelength sweep have different tuning trajectories.

\* \* \* \* \*